(12) United States Patent
Nash et al.

(10) Patent No.: US 11,794,463 B2
(45) Date of Patent: Oct. 24, 2023

(54) WEB MATERIAL APPLICATION SYSTEMS AND METHODS

(71) Applicant: H.B. Fuller Company, St. Paul, MN (US)

(72) Inventors: Jorge A. Nash, Vancouver, WA (US); Orion A. Cavins, Vancouver, WA (US)

(73) Assignee: H.B. Fuller Company, St. Paul, MN (US)

( * ) Notice: Subject to any disclaimer, the term of this patent is extended or adjusted under 35 U.S.C. 154(b) by 186 days.

(21) Appl. No.: 17/450,530

(22) Filed: Oct. 11, 2021

(65) Prior Publication Data
US 2022/0088914 A1    Mar. 24, 2022

Related U.S. Application Data

(63) Continuation of application No. 16/292,995, filed on Mar. 5, 2019, now Pat. No. 11,161,332.

(Continued)

(51) Int. Cl.
*B32B 37/22* (2006.01)
*B32B 38/00* (2006.01)
(Continued)

(52) U.S. Cl.
CPC .............. *B32B 37/22* (2013.01); *B26D 1/405* (2013.01); *B26D 5/20* (2013.01); *B26D 7/14* (2013.01); *B32B 38/0004* (2013.01); *B32B 41/00* (2013.01); *B65H 20/02* (2013.01); *B65H 29/243* (2013.01); *B65H 35/08* (2013.01); *B65H 39/06* (2013.01); *A61F 13/15739* (2013.01);
(Continued)

(58) Field of Classification Search
CPC ..... B32B 37/22; B32B 38/0004; B32B 41/00; B26D 1/405; B26D 5/20; B26D 7/14; B65H 20/02; B65H 29/243; B65H 35/08; B65H 39/06; B65H 2301/51612; B65H 2301/51614; B65H 2406/33; B65H 2406/3612; B65H 2553/51; B65H 2801/57; A61F 13/15739; A61F 13/15764; A61F 13/15772; Y10T 156/1052; Y10T 156/1062
See application file for complete search history.

(56) References Cited

U.S. PATENT DOCUMENTS

| 5,407,513 A * | 4/1995 | Hayden | B32B 38/1825 242/417 |
|---|---|---|---|
| 6,596,108 B2 * | 7/2003 | McCabe | B65H 20/06 156/290 |
| 2004/0112517 A1 * | 6/2004 | Groves | B65H 35/08 156/264 |

* cited by examiner

*Primary Examiner* — George R Koch
*Assistant Examiner* — Christopher C Caillouet
(74) *Attorney, Agent, or Firm* — Daniel Barta; Kirsten Stone

(57) ABSTRACT

A system for cutting a web material and applying the web material on a substrate. The system comprises a feed roll configured to advance a web material. The system includes an anvil roll configured to receive the web material from the feed roll and provide a section of web material having a defined length. The system includes a cutting element configured to cut the web material to form the section of web material. The anvil roll is configured such that the anvil roll surface advances at an anvil roll surface speed. The feed roll is configured to rotate at a first feed roll surface speed that is slower than the anvil roll surface speed and a second feed roll surface speed that is substantially the same as the anvil roll surface speed when the cutting element cuts the web material.

19 Claims, 14 Drawing Sheets

Related U.S. Application Data

(60) Provisional application No. 62/638,576, filed on Mar. 5, 2018.

(51) Int. Cl.
*B65H 20/02* (2006.01)
*B32B 41/00* (2006.01)
*B65H 35/08* (2006.01)
*B26D 7/14* (2006.01)
*B26D 1/40* (2006.01)
*B26D 5/20* (2006.01)
*B65H 29/24* (2006.01)
*B65H 39/06* (2006.01)
*A61F 13/15* (2006.01)

(52) U.S. Cl.
CPC ... *A61F 13/15764* (2013.01); *A61F 13/15772* (2013.01); *B65H 2301/51612* (2013.01); *B65H 2301/51614* (2013.01); *B65H 2406/33* (2013.01); *B65H 2406/3612* (2013.01); *B65H 2553/51* (2013.01); *B65H 2801/57* (2013.01); *Y10T 156/1052* (2015.01); *Y10T 156/1062* (2015.01)

WEB MATERIAL APPLICATION SYSTEMS AND METHODS

This patent application is a Continuation of U.S. patent application Ser. No. 16/292,995, now U.S. Pat. No. 11,161,331, filed Mar. 5, 2019, which claims the benefit of priority to U.S. provisional application No. 62/638,576 filed on Mar. 5, 2018.

FIELD

The present disclosure relates to systems and methods for applying web material to a substrate. More particularly, the present disclosure relates to systems and methods for applying defined sections of web material to a substrate.

BACKGROUND

Various methods and systems exist for applying web material to a substrate. One problem with certain methods and systems is the inability to cut sections of web material, and then apply the sections of web material at a desired location on the substrate as part of a repeated process. Another possible problem is the need to stop production on the system in order to adjust or reconfigure the system to change the sizes or lengths of sections that are to be cut or to re-position the location where the sections are to be placed on the substrate. A further shortcoming is the difficulty of operating such systems with the substrate moving at high speeds relative to the system, such as greater than 600 feet per minute (about 182 meters per minute), while maintaining control of the web material as it is cut and applied to the substrate.

There is a need for a system and/or method for cutting a length of web material into sections having a defined length and then applying the sections to a substrate while maintaining control of the web material as it is cut and applied to the substrate.

SUMMARY

Disclosed herein is a system for cutting a web material and applying the web material on a substrate. The system comprises a feed roll defining a feed roll surface. The feed roll is configured to advance a web material along a predetermined path along the feed roll surface. The system includes an anvil roll defining an anvil roll surface. The anvil roll is configured to receive the web material from the feed roll along the anvil roll surface and provide a section of web material having a defined length. The system includes a cutting element configured to cut the web material along the anvil roll surface to form the section of web material. The anvil roll is configured such that the anvil roll surface advances at an anvil roll surface speed. The feed roll is configured to rotate at a first feed roll surface speed that is slower than the anvil roll surface speed and a second feed roll surface speed that is substantially the same as the anvil roll surface speed when the cutting element cuts the web material. In some aspects, the system is configured to cut a web material and apply the web material on a substrate as a repeated process.

In some aspects, the feed roll is configured to control a feed rate of the web material from the feed roll to the anvil roll such that the web material is substantially free of elastic deformation along a portion of the web material extending between the feed roll and the anvil roll as the cutting element cuts the web material. In some aspects, the first feed roll surface speed and the second feed roll surface speed are configured such that the web material is substantially free of elastic deformation along a portion of the web material extending between the feed roll and the anvil roll as the cutting element cuts the web material. In some aspects, the feed roll is configured to control a feed rate of the web material from the feed roll to the anvil roll such that the feed roll controls the defined length of the section of web material.

In some aspects, the system further comprises a first detector configured to detect a position of the surface of the substrate. In some aspects, the system further comprises an applicator roll configured to receive the section of web material from the anvil roll and apply the section of web material to a surface of a substrate. In some aspects the anvil roll is configured to control a distance between consecutive sections of web material delivered to an applicator roll by controlling a delivery of the sections of web material from the anvil roll to the applicator roll.

In some aspects, the system further comprises a first drive element configured to drive the feed roll, and a second drive element configured to drive the anvil roll independent of the feed roll. In some aspects further comprises a first control element configured to control a first drive element, and a second control element that is configured to control a second drive element independent of the first control element. In some aspects, the feed roll is configured to be driven independent of the anvil roll and is configured to cooperate with the anvil roll to provide sections of web material having a defined length and control a distance between consecutive sections of web material.

Also disclosed herein is a system for applying an elastic web material along a substrate. The system comprises a feed roll configured to advance a web material along a predetermined path. The system includes an anvil roll configured to receive the web material from the feed roll and deliver a section of web material. The system includes a cutting element located proximate the anvil roll. The cutting element is configured to cut the web material to form the section of web material. The system includes an applicator roll configured to receive the section of web material from the anvil roll and apply the section of web material to a surface of a substrate. The feed roll is configured to advance the web material between the feed roll and the anvil roll such that the web material is substantially free of elastic deformation along a portion of the web material between the feed roll and the anvil roll as the cutting element is cutting the web material.

In some aspects, the anvil roll is configured to control a distance between consecutive sections of web material delivered to the applicator roll. In some aspects, the feed roll defines an outer surface, and the feed roll is configured to control a feed rate of the web material from the feed roll to the anvil roll by controlling a tangential speed of the outer surface of the feed roll. In some aspects, the feed roll is configured to control a feed rate of the web material from the feed roll to the anvil roll such that the portion of web material extending between the feed roll and the anvil roll is substantially free of elastic deformation as the cutting element is cutting the web material. In some aspects, the feed roll feed roll and anvil roll cooperate to control a distance between consecutive sections of web material by controlling a delivery of the sections of web material from the anvil roll to the applicator roll while the feed roll controls a feed rate of the web material to the anvil roll. In some aspects, the feed roll is configured to rotate at a first tangential speed that is less than a tangential speed of the anvil roll, and a second tangential speed that is substantially the same as the tangential speed of the anvil roll as the cutting element is cutting the web material.

Also disclosed herein is a method of applying a web material to a substrate. The method comprises feeding a web material along an outer surface of a feed roll to an outer surface of an anvil roll. The method includes cutting the web material as the web material is positioned along the outer surface of the anvil roll, to form a section of web material. The method includes advancing the section of web material from the outer surface of the anvil roll to an outer surface of an applicator roll. The method includes applying the section of web material to a surface of a substrate with the applicator roll. The method includes controlling a speed of the surface of the feed roll between a first feed roll surface speed that is slower than a first anvil roll surface speed and a second feed roll surface speed that is substantially the same as the first anvil roll surface speed during the step of cutting the web material.

In some aspects, the controlling step includes increasing the speed of the outer surface of the feed roll from the first feed roll surface speed to the second feed roll surface speed before the step of cutting the web material such that the web material is substantially free of elastic deformation during the step of cutting the web material. In some aspects, a feed rate of the web material from the feed roll to the anvil roll is increased before the step of cutting the web material by increasing the speed of the surface of the feed roll from the first (slower) feed roll surface speed to the second (faster) feed roll surface speed. In some aspects, the controlling step reduces a tension along a portion of web material extending between the feed roll and the anvil roll such that the portion of web material between the feed roll and the anvil roll is substantially free of elastic deformation along a direction from the feed roll to the anvil roll.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

DETAILED DESCRIPTION

Disclosed herein are systems and methods for cutting a length of web material into defined sections and then applying the cut sections of web material to a substrate or a series of substrates. The length of each section and the position of the sections placed on the substrate are adjustable with these methods and systems. Further disclosed herein are systems and methods for cutting elastic material into defined sections of suitable lengths and applying the cut sections of elastic material to a substrate or series of substrates. The systems and methods disclosed herein can be used to cut an elastic material into sections of defined lengths while maintaining control of the elastic material on a predetermined path through the system. The length of web material may be cut and applied to a substrate as part of a continuous process, such as while the length of web material is fed to the system at a constant feed rate from a feed source, such as an unwind roll. The web material may be cut and applied to a substrate as part of an intermittent process, such as a process that includes starting and stopping the feed rate of the web material as it is fed to the system from a feed source.

The cut sections of material are applied such that they are placed at a desired location on a substrate, such as a surface of the substrate. The feed rate of the material and the timing of the cutting can be used to control the length of the sections and placement of the sections on the substrate. In certain embodiments, changes in the length of the sections of material being cut can be made without mechanical adjustments of the basic components of the system. For example, the changes in the length and/or placement of each section may be made by controlling the timing and coordination of the various components of the system during operation.

Figure 1:
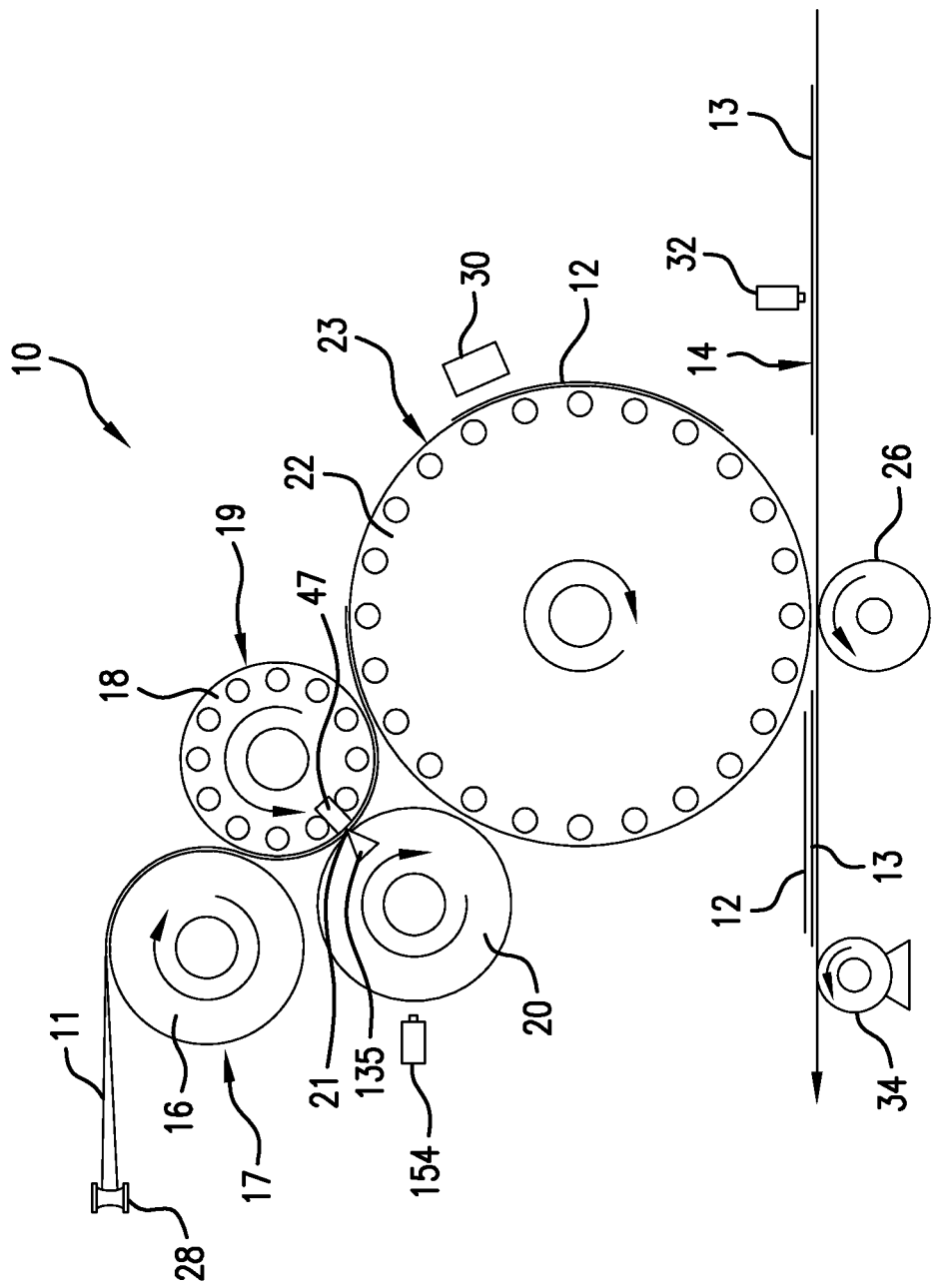
FIG. 1 is a schematic view of a system for applying a material to a substrate, in accordance with some embodiments.

FIG. 1 shows an overall schematic of a system 10 for applying material on a substrate. As shown in FIG. 1, the system 10 includes a feed roll 16, an anvil roll 18, and a cutting element 20. As shown, the system 10 may also include an applicator roll 22. The feed roll 16 defines an outer surface 17, the anvil roll 18 defines an outer surface 19, and the applicator roll 22 defines an outer surface 23. The anvil roll 18 include an anvil 47. The cutting element 20 includes a cutting feature 135. As shown in FIG. 1, the system 10 may include various additional features such as a backup roll 26, a guide roller 28, an activation element 30, a sensor 32, an encoder 34, and a feed sensor 154.

In general, the system 10 advances a material having a length and a width, such as a web material 11, from a feed supply (not shown), cuts the web material 11 into sections 12 of defined length at a cut point 21, and applies the sections 12 onto a substrate 13. The system 10 can be operated to advance the web material 11 from a feed supply, advance the web material 11 along a predetermined path along the outer surface 17 of the feed roll 16, along the outer surface 19 of the anvil roll 18, and past the cutting element 20 where the material 11 is cut into sections 12. The sections 12 may then be positioned along the outer surface 23 of the applicator roll 22. The applicator roll 22 may apply the sections 12 of material onto the substrate 13. The system 10 can be used to apply each of the sections 12 to a desired position on the substrate, for example along a surface 14 of the substrate 13. The system 10 can be used to cut and apply web material 11 that is elastic. The system 10 can be operated to cut and apply elastic material while controlling the elastic material free from elastic deformation at suitable times while the elastic material advances along the predetermined path. For example, the system 10 may inhibit the elastic material from being elastic deformed as the elastic material is being cut. The system is configured to control the rotational speed of the feed roll 16 such that tangential speed of the outer surface of the feed roll 16 matches, or is substantially the same as the tangential speed of the outer surface of the anvil roll 18 when the material is being cut.

As used herein, an elastic material is a material that can undergo at least a 5 percent deformation along a first direction without the material breaking. That is, an elastic material is a material that when tension is applied along a first direction, the material can stretch greater than 5 percent the original length in the first direction without the material breaking or becoming irreversibly deformed along the first direction.

Figure 2A:
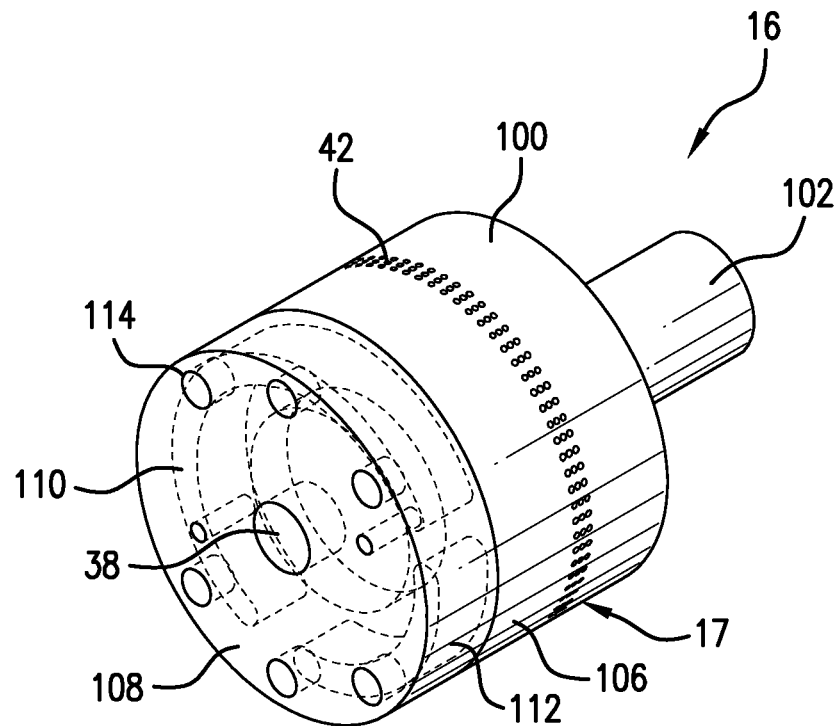
FIGS. 2A and 2B are perspective and front cut away views respectively of a feed roll of the system of FIG. 1, in accordance with some embodiments.
Figure 2B:
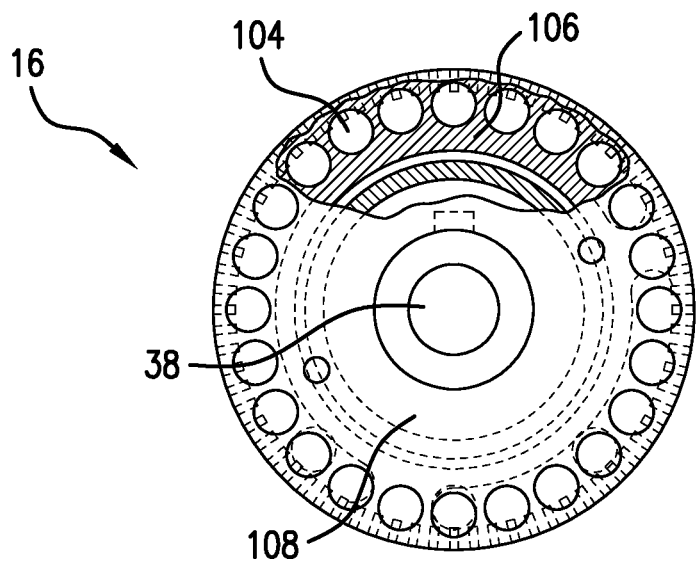

FIGS. 2A and 2B are perspective and front cut away views respectively of the feed roll 16 shown in FIG. 1, to show additional features. The feed roll 16 defines a central axis 38. The feed roll 16 comprises a hub 100 which is mounted on a first shaft 102. The first shaft 102 may be connected to the hub 100 through the central axis 38 of the feed roll 16. In some embodiments, the hub 100 may be configured to rotate about the central axis 38.

As shown in FIGS. 2A and 2B, in some embodiments, the hub 100 may define a series of axially extended tubes 104 defined partially through the hub 100 and formed through a first end wall 106 of the hub 100. The tubes 104 are positioned near the periphery of the hub 100 and are spaced circumferentially and communicate with holes 42 that are defined in the outer surface 17 of the feed roll 16. The holes 42 extend radially into the hub 100 from the outer surface 17. Mounted against the first end wall 106 of the hub 100 is a manifold 108. The manifold 108 has a grooved arcuate slot 110 extending about 130 degrees to about 360 degrees about an end wall 112 of the manifold 108. The end wall 112 of the manifold 108 is adjacent axially to the first end wall 106 of the hub 100.

The manifold 108 is supported in a fixed position by a bracket 114, and the slot 110 is positioned adjacent the path of the axially extended tubes 104 of the hub 100. During the rotation of the hub 100, the axially extended tubes 104 are covered by the end wall 112 of the manifold 108. As the hub 100 rotates, the axially extended tubes 104 become aligned or substantially aligned with the slot 110, and the axially extended tubes 104 serially come into fluid communication with the slot 110. Air may be drawn through the slot 110 and through the axially extended tubes 104 as they come into fluid communication with the slot 110, which may then draw air through the holes 42. This may create an area of low pressure along the outer surface 17 of the feed roll 16. For example, between the outer surface 17 and a material along the outer surface 17, such as the web material 11 shown in FIG. 1. The pressure created inside the holes 42 is less than atmospheric (e.g., a vacuum). The atmospheric pressure helps to hold the web material against the outer surface 17 of the feed roll 16 in the area of the holes 42 as the hub 100 rotates the axially extended tubes 104 along the area of the manifold 108 having the slot 110. This helps to inhibit slippage of the web material 11 relative to the outer surface 17 of the feed roll 16. In some embodiments, inhibiting or reducing slippage helps to move the material along with the outer surface 17 of the feed roll 16 as the hub 100 of the feed roll 16 rotates. In some instances, the feed roll 16 moves the material at a linear speed that is the same as the tangential speed of the outer surface 17 of the feed roll 16 as the hub 100 rotates.

The vacuum created along the outer surface 17 through the holes 42 holds the leading edge of the material on the feed roll 16 until it can be transferred, such as to the anvil roll 18 shown in FIG. 1. As the feed roll 16 rotates, the material advances along the section of the outer surface 17 of the feed roll 16 that has a vacuum formed in the holes 42. The leading edge of the material can separate from the outer surface 17 of the feed roll 16. Gravity, a positive or atmospheric pressure, and/or engagement with the anvil roll 18, can cause the leading edge of the material to advance to the anvil roll 18.

The feed roll 16 is formed of materials including metal, plastic, or a composite of material. The feed roll 16 may be coated with material having a coefficient of friction sufficient to aid in controlling the web material 11 in position along the outer surface 17. In some embodiments, the hub 100 may include a material along the peripheral surface that forms the outer surface 17 of the feed roll 16, which may have a high coefficient of friction to provide traction with a web material disposed along the hub 100.

Figure 3:
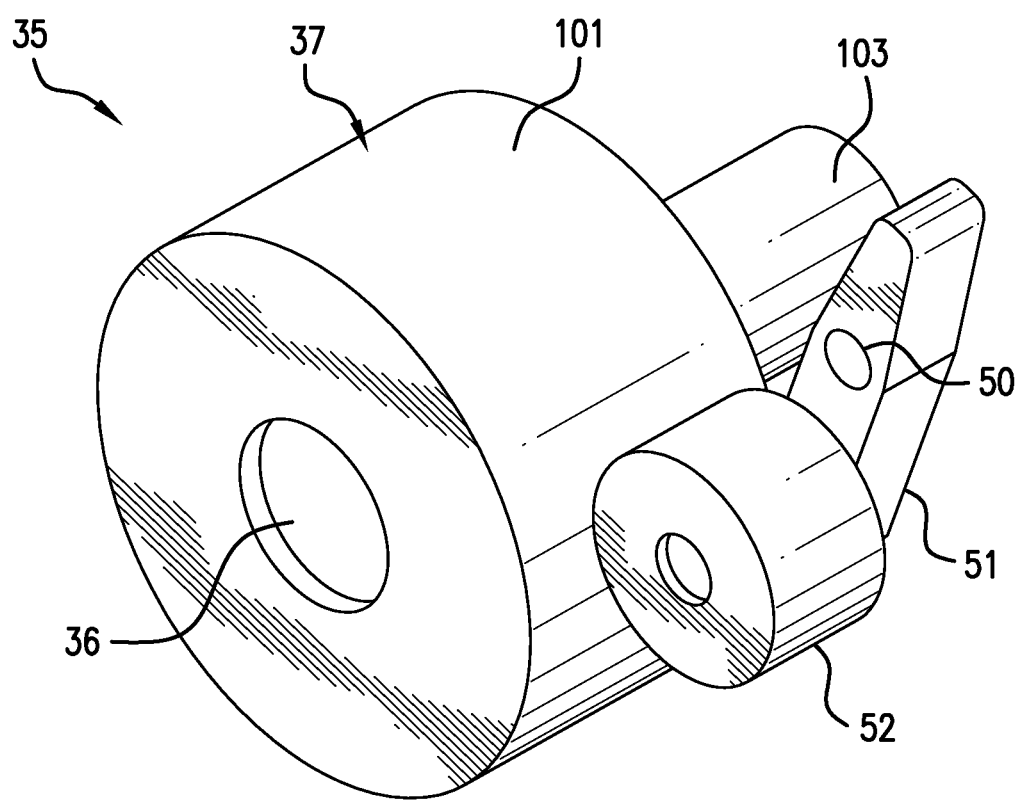
FIG. 3 is a perspective view of an alternative example of a feed roll of the system of FIG. 1, in accordance with some embodiments.

FIG. 3 is a perspective view of an alternative embodiment of a feed roll 35 that may be used in the system 10 of FIG. 1. As shown in FIG. 3, the feed roll 35 comprises a hub 101 which is mounted to a first shaft 103. The first shaft 103 may be connected to the hub 101 through a central axis 36 of the feed roll 35. The hub 101 defines an outer surface 37 of the feed roll 36. In operation, the hub 101 rotates and advance outer surface 37 which defines a tangential speed of the feed roll 35. In some embodiments, the hub 101 is formed of a material having a coefficient of friction of from about 0.5, about 0.6, or about 0.7, to about 0.8, or about 0.9, or a coefficient of friction between any pair of the foregoing values, with the web material 11 to aid in advancing the web material 11.

As shown in FIG. 3, a pressure roll 52 may be located proximate the feed roll. The pressure roll 52 may be used to bias and/or hold a web material against the outer surface 37 of the feed roll 35. The pressure roll 52 may be rotatably mounted on a lever 51. The lever 51 may be mounted on a pin 50. The pressure roll 52 may be biased, for example by a spring positioned between the pin 50 and the lever 51, to urge the pressure roll 52 into engagement with the web material to hold the web material against the feed roll 35. The pressure roll 52 can rotate with the feed roll 35, and help to hold the web material against the feed roll 35 as the feed roll 35 turns.

Figure 4A:
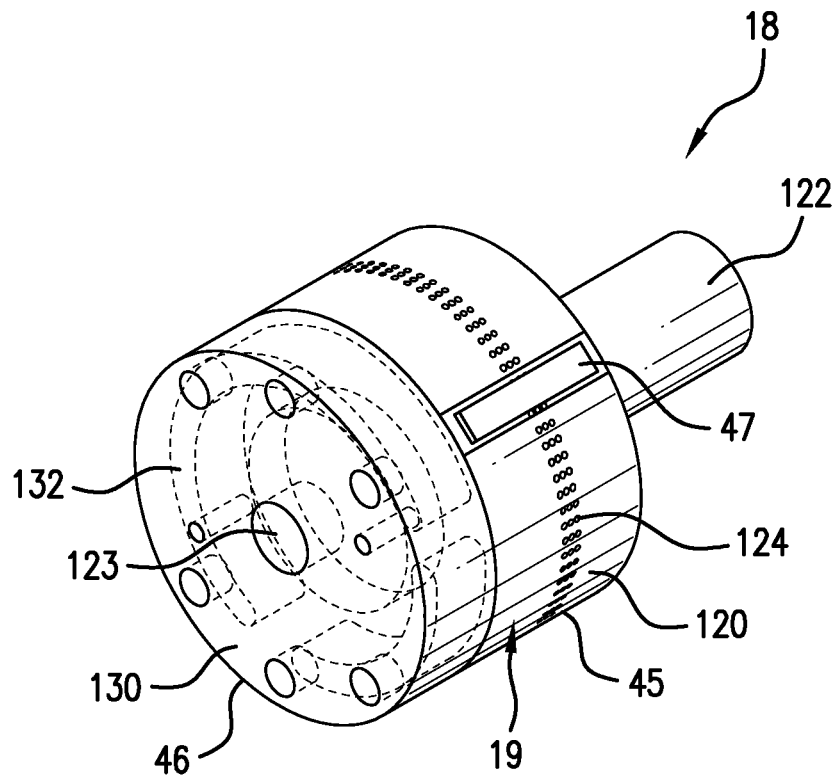
FIGS. 4A and 4B are perspective and front cut away views of an anvil roll of the system of FIG. 1, in accordance with some embodiments.
Figure 4B:
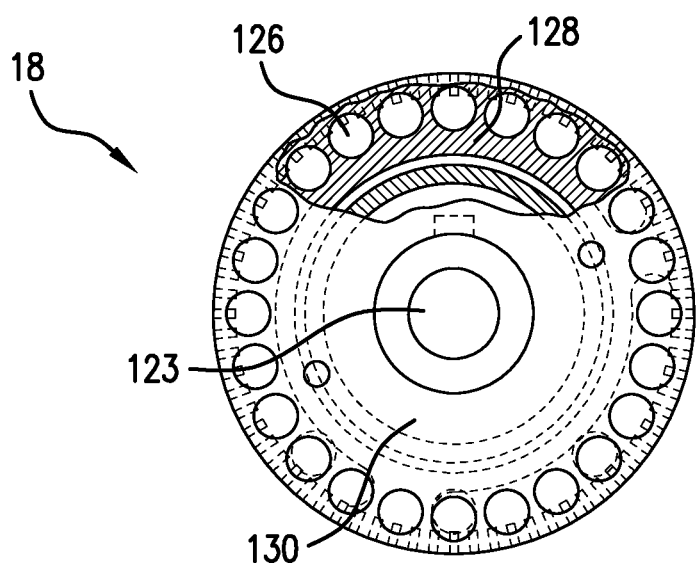

FIGS. 4A and 4B are perspective and front cut away views of the anvil roll 18 shown in FIG. 1. The anvil roll 18 has a first side 45, a second side 46, and a central axis 123. As shown in FIGS. 4A and 4B, in some embodiments, the anvil roll 18 comprises a hub 120 mounted on a shaft 122. In some embodiments, the anvil roll 18 includes the anvil 47, which may be a hardened insert, along the outer surface 19 of the anvil roll 18. The hub 120 is configured to rotate about the central axis 123 of the anvil roll 18. In some embodiments, the anvil roll 18 may include additional features to control a position of the web material 11 relative to the outer surface 19 of the anvil roll 18.

In some embodiments, the anvil roll 18 includes similar components as previously described with respect to the feed roll 16 in FIGS. 2A and 2B for providing a vacuum along the outer surface 19 of the anvil roll 18. For example, the outer surface 19 of the anvil roll 18 may include a series of holes 124 in fluid communication with axially extended tubes 126 formed through a side wall 128 of the hub 120. The axially extended tubes 126 are positioned circumferentially about the hub 120 and during rotation of the hub 120, communicate with a slot 132 in a manifold 130 positioned axially against the hub 120. The slot 132 may extend about 130 to 360 degrees about the circumference of the anvil roll 18. A vacuum can be formed through the slot 132, the axially extended tubes 126, and through the holes 124. The vacuum holds a length of material along the outer surface 19 of the anvil roll 18, for example at the point where the material is received from the feed roll 16, and/or from the point of cut to the area of transfer to the next component, such as the applicator roll 22 or a substrate 13, as shown in FIG. 1.

In some embodiments, the outer surface 19 of the anvil roll 18 may include a material that has a low coefficient of friction, for example a fluoroethylene such as that sold under the trade name Teflon™, to allow slippage with a web material disposed on the anvil roll 18.

Figure 5:
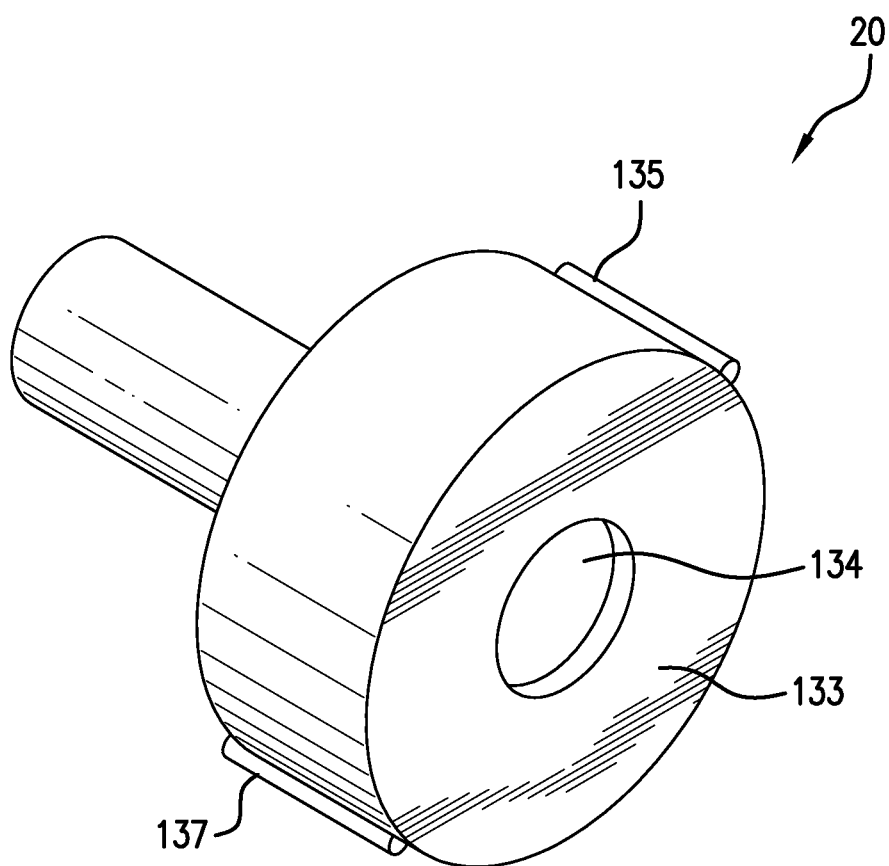
FIG. 5 is a perspective view of a cutting element of the system of FIG. 1, in accordance with some embodiments.

FIG. 5 is a perspective view of the cutting element 20 shown in FIG. 1. As shown, the cutting element 20 may be a hub 133 configured to rotate about a central axis 134. A cutting feature 135, such as a blade or a heated wire, may be positioned such that as the cutting element 20 rotates, the cutting feature 135 comes into contact with the material and can cut the material. For example, the cutting element 20 may be a rotary knife. The cutting feature 135 extends the length of the hub 133, with a blade forming the end of the cutting feature 135, such as a cutting edge. When placed in the hub 133, as shown in FIG. 5, the cutting feature 135 extends beyond the periphery of the hub 133 and can penetrate through the thickness of a material to be cut. As shown in FIG. 5, in some embodiments, the cutting element 20 may include a second cutting feature 137 such that the cutting element 20 can effect more than one cut for each full rotation of the hub 133. In certain embodiments, the anvil roll 18 has a different circumference than that of the cutting element 20 so that the location where the cutting feature 135 contacts the outer surface 19 of the anvil roll 18 varies for each cut, thereby extending the life of the anvil roll 18.

Figure 6A:
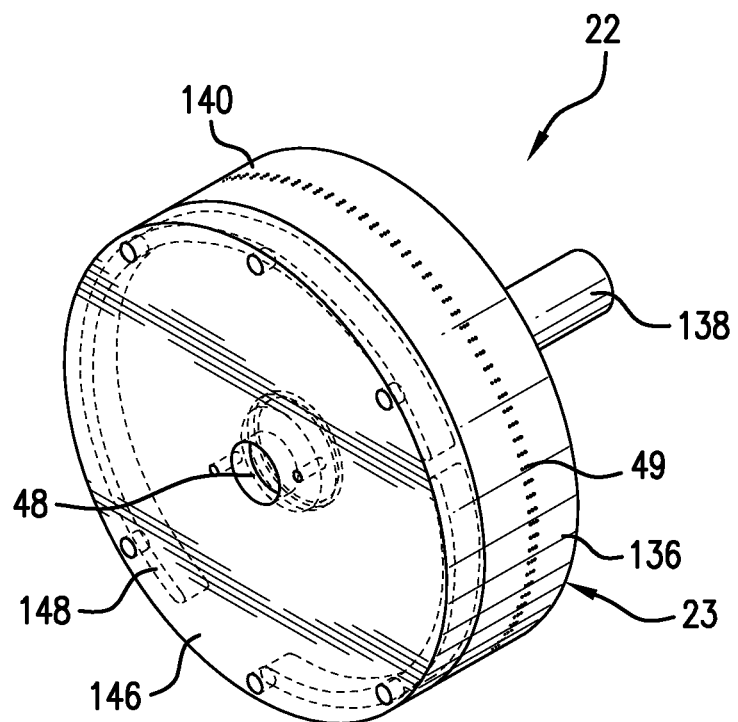
FIGS. 6A and 6B are perspective views of an applicator roll of the system of FIG. 1, in accordance with some embodiments.
Figure 6B:
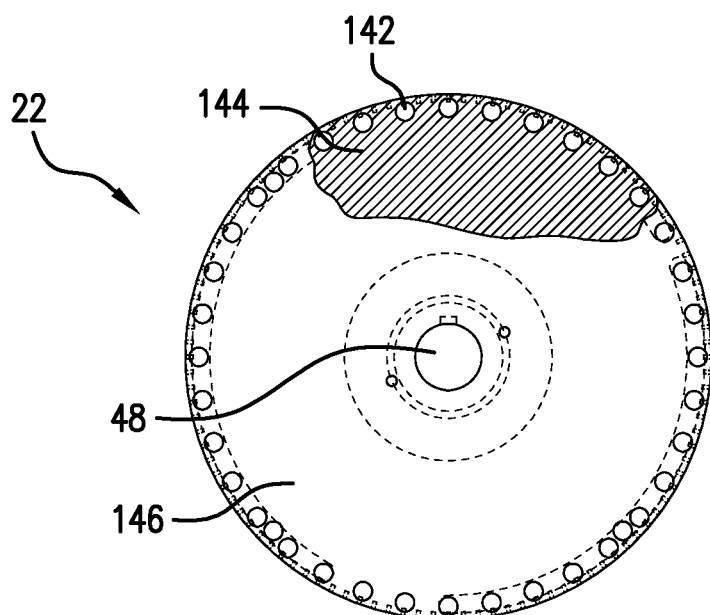

FIGS. 6A and 6B are perspective and front cut away views of the applicator roll 22 shown in FIG. 1. As shown, in some embodiments, the applicator roll 22 comprises a hub 136 mounted on a shaft 138 along a central axis 48. In some embodiments, the applicator roll 22 includes similar components as previously described on the feed roll 16 with reference to FIG. 2 for providing a vacuum along the outer surface 23 of the applicator roll 22. For example, the outer surface 23 of the applicator roll 22 may include a series of holes 140 in fluid communication with axially extended tubes 142 defined through a side wall 144 of the hub 136. The axially extended tubes 142 are positioned circumferentially about the hub 136. During rotation of the hub 136, the axially extended tubes 142 communicate with a slot 148 in a manifold 146 that is positioned axially against the side wall 144. Air may be drawn through the holes 124, through the axially extended tubes 142 and though the slot 148. Drawing air through the holes 142 may provide a vacuum along a portion of the outer surface 23. The vacuum may hold a length of material along the outer surface 23 of the applicator roll 22, for example from the point where the material is received from the anvil roll 18 to the area of transfer to a subsequent component, such as the substrate 13 shown in FIG. 1.

Figure 7:
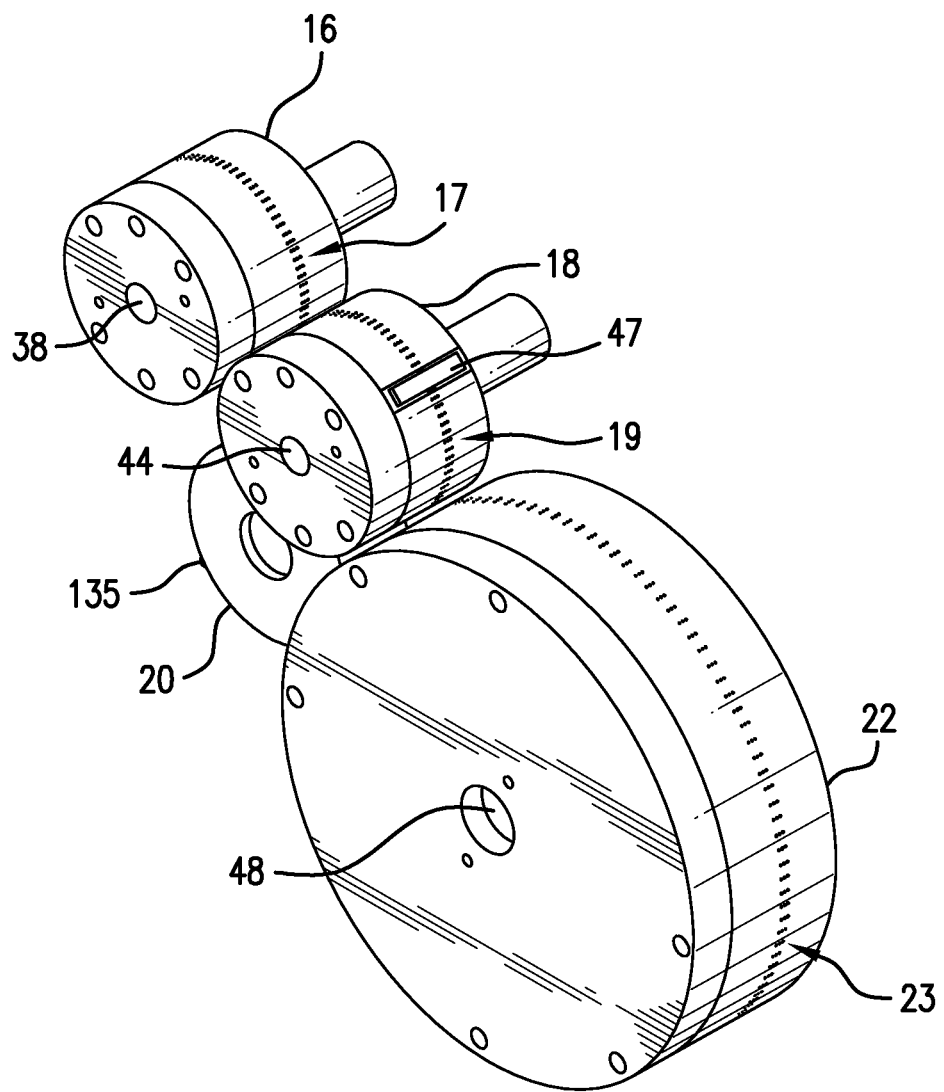
FIG. 7 is a perspective view of certain components of the system shown in FIG. 1, in accordance with some embodiments.

FIG. 7 is a perspective view of certain components of the system 10 shown in FIG. 1 positioned relative to one another in the system 10, according to some embodiments. As shown in FIG. 7, the feed roll 16 is generally shaped as a cylinder with the outer surface 17 defining the circumference and width of the cylinder. The feed roll 16 may be operably mounted, for example along the central axis 38 of the feed roll 16. In the example shown in FIG. 7, the feed roll 16 is configured to turn clockwise in a direction tangent to the circumference of the feed roll 16 when in operation. In examples of the system 10, arranged in an alternative configuration, such as a mirror image, the direction of turn for the various components may be in the counter clockwise direction.

The feed roll 16 is configured to receive a material, such as the web material 11 shown in FIG. 1 along the outer surface 17. The outer surface 17 of the feed roll 16 defines a path that the web material 11 travels along around the circumference of the feed roll 16. For example, the web material 11 can be fed to the outer surface 17 of the fed roll 16 and travel around the circumference of the feed roll 16 as the feed roll 16 rotates.

As shown in FIG. 7, the anvil roll 18 is generally shaped as a cylinder with the outer surface 19 defining the circumference and width of the cylinder. The anvil roll 18 may be operably mounted, for example along the central axis 44 of the anvil roll 18. In the example shown in FIG. 7, the anvil roll 18 is configured to turn clockwise in a direction tangent to the circumference of the anvil roll 18 when in operation. In some embodiments, the anvil roll may include features such as the anvil 47 for engaging the cutting feature 135 associated with the cutting element 20. The anvil 47 may be used to guide the cutting feature 135 and/or prevent the cutting feature 135 from compromising the outer surface 19 of the anvil roll 18.

The anvil roll 18 is configured to receive a material, such as the web material 11 shown in FIG. 1 along the outer surface 19. The outer surface 19 of the anvil roll 18 defines a path that the web material 11 travels along around the circumference of the anvil roll 18. The web material 11 can be fed to the outer surface 19 of the anvil roll 18 and advanced along the circumference of the anvil roll 18 as the anvil roll 18 rotates.

As shown in FIG. 7, the cutting element 20 is positioned proximate the anvil roll 18. The cutting element 20 is configured to cut material positioned along the anvil roll 18 at repeatable intervals to produce sections of defined lengths. The cutting element 20 includes the cutting feature 135. The cutting feature 135 may be a rotary knife that cuts material as the rotary knife turns.

As shown in FIG. 7, the applicator roll 22 is generally shaped as a cylinder with the outer surface 23 defining the circumference and width of the cylinder. The applicator roll 22 may be operably mounted to rotate around the central axis 48 of the applicator roll 22. In the example shown in FIG. 7, the applicator roll 22 is configured to turn in a clockwise direction tangent to the circumference of the applicator roll 22 when in operation. The applicator roll 22 is configured to receive a material, such as the sections 12 of the web material 11 shown in FIG. 1 along the outer surface 23. The applicator roll 22 holds the sections 12 of the web material 11 along the outer surface 23 and the applicator roll 22 applies the sections 12 of the web material 11 onto a substrate.

Figure 8:
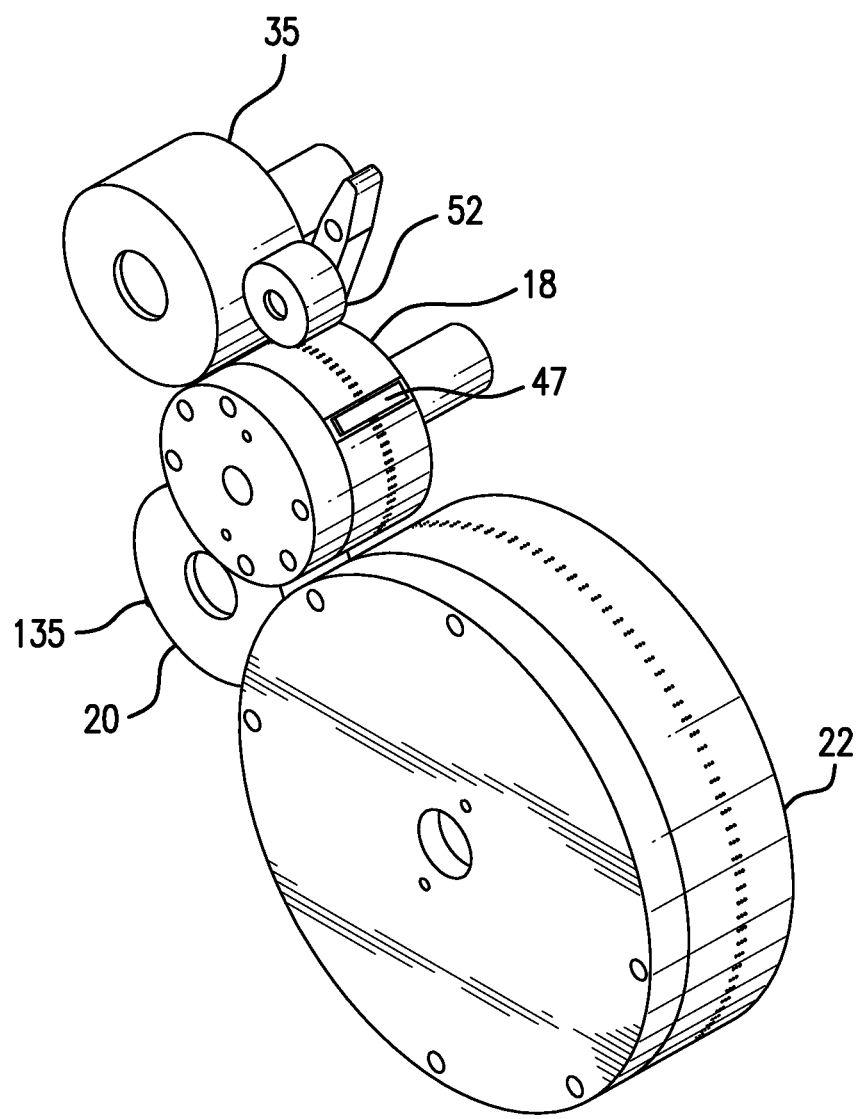
FIG. 8 is a perspective view of certain components of the system shown in FIG. 1, in accordance with further embodiments.

FIG. 8 is a perspective view of an alternative embodiment of the system 10 shown in FIGS. 1 and 7, with the feed roll 35 and pressure roll 52 shown in FIG. 3, to show the various components of the system 10 positioned relative to one another. As shown in FIG. 8, the pressure roll 52 is positioned proximate to the feed roll 35. The pressure roll 52 may be positioned such that the pressure roll 52 helps maintain the web material along the feed roll 35 until the point where the web material is transferred to the anvil roll 18. The anvil roll 18 includes features such as a vacuum system, described with reference to FIGS. 4A and 4B, to maintain the web material along the anvil roll 18. The vacuum system can also help the anvil roll 18 pull the web material from the feed roll 35 and the pressure roll 52. The anvil roll 18 maintains the web material in position as the anvil roll 18 and the cutting element 20 rotate. As the anvil roll 18 and the cutting element 20 rotate, the anvil 47 and the cutting feature 135 align and come in contact to cut the web material positioned along the anvil roll 18. The web material is cut into sections which are then passed to the applicator roll 22.

Figure 9:
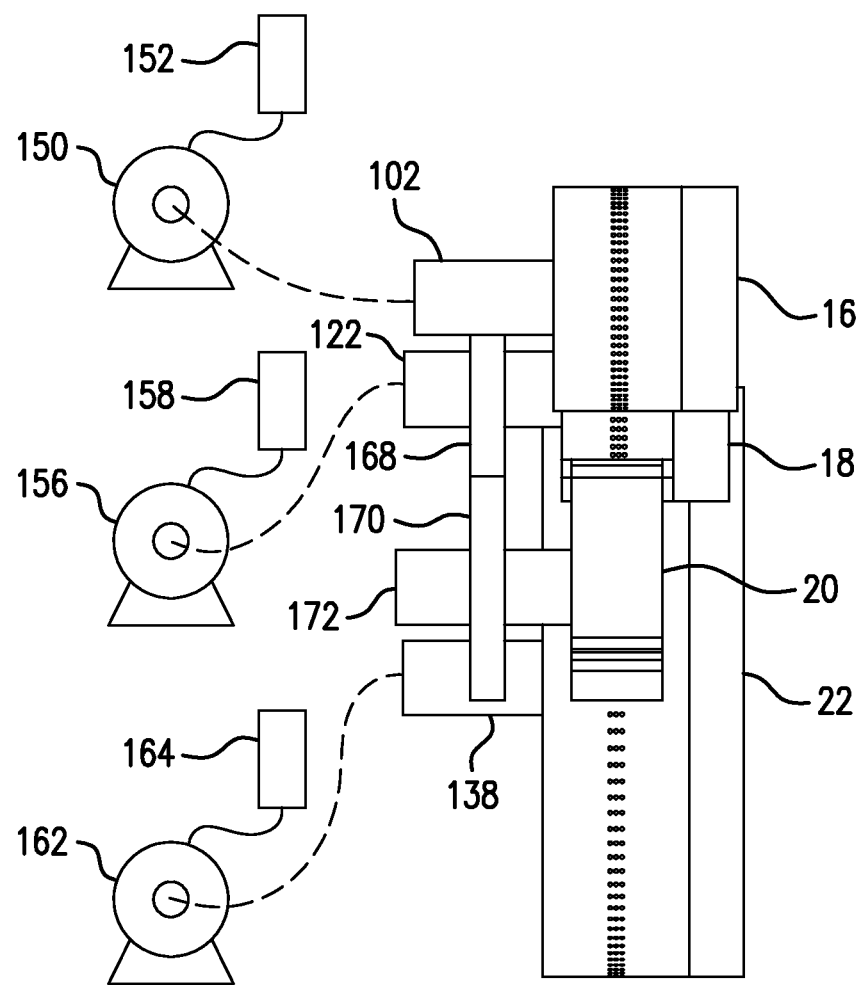
FIG. 9 is a side view of certain components of the system shown in FIG. 1, in accordance with some embodiments.

FIG. 9 is a side view of the system 10 shown in FIG. 1, to show additional features. As shown in FIG. 9, a first motor 150, controlled through a first motor controller 152, drives the shaft 102 that drives the feed roll 16. A second motor 156, controlled through a second motor controller 158 drives the shaft 122 that drives the anvil roll 18. As shown, a third motor 162, controlled through a third motor controller 164 drives the shaft 138 that drives the applicator roll 22. As shown in FIG. 9, the shaft 122 that is driven by the second motor 156 is connected to a first gear 168. The first gear 168 may be meshed to a second gear 170.

As shown in FIG. 9, the feed roll 16, the anvil roll 18, and the applicator roll 22 each have separate drive means for rotating. In some embodiments, the rotational speed of each roll can be adjusted by the use of the motor controllers. For example, the first motor controller 152 and the second motor controller 158 control the rotational speed of the feed roll 16 and of the anvil roll 18 with respect to each other. In this arrangement, the tangential speed of the outer surface 17 of the feed roll 16 can be controlled independent of the tangential speed of the outer surface 19 of the anvil roll 18. In other words, the tangential speed of the outer surface 17 of the feed roll 16 can be driven faster or slower relative to the tangential speed of the outer surface 19 of the anvil roll 18. The anvil roll 18 can also be driven independent of the feed roll 16 such that the anvil roll 18 can turn at a tangential speed that is faster or slower relative to the tangential speed of the outer surface 17 of the feed roll 16.

The timing of the cutting of the web material 11 and the length of the sections 12 of material may be adjusted, for example by controlling the tangential speed of the outer surface of the rolls with respect to one another. In some embodiments, the length of each section of web material that is cut is controlled by the relationship between the tangential speed of the feed roll 16 and/or the anvil roll 18 and the trigger rate of the cutting element 20. In some examples, such as in the case of a rotary knife, the trigger rate corresponds to the tangential speed of the cutting element 20 and the circumference of the cutting element 20. For example, by increasing the tangential speed of the feed roll 16 in relation to the tangential speed of the anvil roll 18 and the cutting element, a greater length of web material 11 can be advanced in between each cut, resulting in longer sections 12.

In some embodiments, a space or gap between consecutive sections 12 of web material 11 on the applicator roll 22 may be controlled by decreasing the tangential speeds of the feed roll 16 and/or the anvil roll 18 in relation to tangential speed of the applicator roll 22. For example, the distance between consecutive sections 12 of material may be increased by further decreasing the tangential speeds of the feed roll 16 and/or the anvil roll 18 in relation to tangential speed of the applicator roll 22. For example, by starting and or increasing the speed of the feed roll 16 and/or the anvil roll 18 before or when the web material is being cut, followed by stopping or decreasing the tangential speed of the feed roll 16 and/or the anvil roll between consecutive cuts, advancing the sections 12 to the applicator roll can be delayed in between cuts, such that a gap is formed between each of the consecutive sections 12. The size of the gap between each of the sections 12 as the sections 12 are passed to the applicator roll 22 can also be controlled. Thus the collaboration between the motor controls of the feed roll 16 and the anvil roll 18 can be used to determine the length and placement of the sections 12 of material on the applicator roll 22 and the substrate 13.

The system 10 shown in FIG. 1, may be used to cut a material such as the web material 11. In some instances, a process for operating the system 10 includes advancing web material 11 through the system 10, cutting the web material 11 into sections 12 of defined length, and applying the sections 12 to a substrate 13 or series of substrates. The system 10 may be used to cut, for example, a web material 11 that has an adhesive disposed on a first side of the web material 11.

In operation, the system 10 advances the web material 11 from the feed supply and around the feed roll 16. In some embodiments, the guide roller 28 guides the web material 11 onto the feed roll 16, and may be used to feed the web material 11 onto a predetermined path on the feed roll 16. In instances where the system 10 is used to cut web material 11 having an adhesive disposed along a first side of the web material 11, the web material 11 may be fed onto the feed roll 16 with a second side of the web material 11, that does not have adhesive disposed on it, directed toward the outer surface 17 of the feed roll 16. The feed roll 16 may include a vacuum element (such as described with reference to FIGS. 2A and 2B) for maintaining the web material 11 in relation to the outer surface 17 of the feed roll 16, and reducing slip in relation to the feed roll 16. When the system 10 is operating, the web material 11 may contact from about 1 degree, about 10 degrees, about 20 degrees, or about 30 degrees of the outer surface 19, to about 90, about 180 degrees, about 270 degrees, or about 300 degrees of the circumference of the outer surface 17 of the feed roll 16, or a length between any pair of the foregoing values, although additional lengths are contemplated.

After passing around the feed roll 16, the web material 11 advances to the anvil roll 18. The web material 11 may extend from the feed roll 16 to the anvil roll 18, travel along the outer surface 19 of the anvil roll 18 and past the cutting element 20. The cutting element 20 may be positioned proximate the anvil roll 18. The space between the anvil roll 18 and the cutting element 20 defines a path from the feed roll 16 to the applicator roll 22. In certain embodiments, the web material 11 contacts the outer surface 19 of the anvil roll 18 proximate to the cut point 21. In certain embodiments, the web material 11 contacts from about 30 degrees, about 40 degrees, about 50 degrees, or about 60 degrees of the outer surface 19, to about 90, about 120 degrees, about 180 degrees, or about 270 degrees, of the circumference of the outer surface 19 of the anvil roll 18, or a length between any pair of the foregoing values, although additional lengths are contemplated.

The web material 11 is cut at the cut point 21 to sections 12 of the desired defined lengths. The cut point 21 is defined at a point of engagement between the cutting element 20 and the anvil roll 18. Cutting the web material 11 into sections 12 may be accomplished by the cutting feature 135, as shown in FIG. 4. The cutting feature 135 engages with the anvil roll 18 and affects a cut of the web material 11 between the cutting feature 135 and anvil 47. The defined length of each of the sections 12 may be controlled by timing the instant of cut once the desired length of web material 11 has passed the cut point.

In some embodiments, the sections 12 are positioned on the applicator roll 22 after the web material 11 is cut. In some embodiments, a leading edge of the web material 11 may be positioned on the applicator roll 22 and a portion of the web material 11 extends between the anvil roll 18 and the applicator roll 22 before each of the sections 12 is cut. For example, the leading edge of the of the web material 11 may be advanced from the outer surface 19 of the anvil roll 18 to the outer surface 23 of the applicator roll 22. As the applicator roll 22 rotates, it continues to pick up more of the length of the material. Once a suitable length of web material 11 has been transferred from the anvil roll 18 to the applicator roll 22, the cutting element 20 and anvil roll 18 engage the web material 11, thereby cutting the web material 11. At this point, the trailing end of each section 12 is transferred onto the applicator roll 22. The anvil roll 18 holds the leading edge of the next section of web material 11 until it too is transferred onto the applicator roll 22.

In some embodiments, the activation element 30 may be used to condition the web material 11 before the web material 11 is applied to the substrate 13. For example, the web material 11 may have an adhesive material disposed on a surface of the web material 11. In some instances, such as if the adhesive material is heat activated, the activation element 30 may be used to heat the adhesive material, such as by heating the adhesive material with an infrared heat source or a supply of heated air. In a further example, the activation element 30 may activate the adhesive material by providing alternative sources of energy, such as ultraviolet radiation, to the adhesive material. A further example may be activating the adhesive with moisture in the case of a moisture activated adhesive. The activation element 30, may be positioned such that the adhesive disposed on the web material 11 is activated after the web material 11 is past the anvil roll 18. The adhesive disposed on the web material 11 may be activated after the web material 11 has been cut into sections 12. In some embodiments, the system may be used to apply adhesive materials such as pressure sensitive materials or tapes that do not require the use of an activation element 30.

In some embodiments, to position the sections 12 of web material 11 properly on the substrate 13, the sensor 32 and/or the encoder 34 are positioned along the path of the substrate 13. The signal from the sensor 32 and the encoder 34, and the signal from the cutting element 20 are all received by a system controller (not shown) such as an integrated control system (ICS). The system controller receives information about the position and speed of the substrate, for example, by measuring the speed of the surface 14 of the substrate 13 from the sensor 32 and/or the encoder 34, both of which may be positioned along the substrate feed path. The placement upon the substrate 13 can be controlled by the system controller, which operates the third motor controller 164 and the third motor 162 that drive the applicator roll 23, as shown in FIG. 7. The tangential speed of the outer surface 23 of the applicator roll 22 is matched to the line speed of the substrate 13 by the third motor controller 164 which controls the third motor 162 which drives the applicator roll 22. The placement of the web material 11 on the applicator roll outer surface 23 can be controlled by the system controller, which operates the first motor controller 152 and the first motor 150 that drive the feed roll 16, and the second motor controller 158 and second motor 156 that drive the anvil roll 18, as shown in FIG. 9.

It is contemplated that in some applications, the applicator roll 22 can be mechanically connected to a conveyor that is used to advance the substrate 13 through the system 10. The speed of the applicator roll 22 can be set by the operator. In other words, the applicator roll 22 speed can be locked to the speed of the substrate 13 by matching it to the speed of the conveyer and then measured by the encoder 34. The applicator roll 22 can rotate at a constant rate, and the system controller can change the speed of the feed roll 16 and/or the anvil roll 18 accordingly. The system 10 may control the transfer of the web material 11 to the applicator roll 22 and once the web material 11 is on the applicator roll 22, the transfer of the section 12 of web material 11 to the substrate 13 is locked in by the mechanical linkage of the applicator roll 22 to the conveyor.

In some embodiments, the sensor 32 may determine the position of the substrate 13 and/or a distance of a surface 14 of the substrate 13 relative to the system 10. The sensor 32 may also determine a speed the substrate 13 is traveling relative to the system 10. The backup roll 26 may be used to maintain a position of the substrate 13 relative to the system 10. The backup roll 26 may bias the substrate 13 toward the applicator roll 22.

The system controller can generate control signals to the first and second motor controllers 152 and 158 respectively to synchronize together the feed of the material, the trigger of the cutting element 20, and the position of the substrate 13 (or registry indicia) so that the speeds of the various components of the system 10 are set at the correct level to achieve the desired cutting. For instance, the system 10 can provide feedback for adjusting the placement position of the sections 12 on substrates if there is an irregularity or inconsistent feed of individual substrates within a single production run.

The sensor 32 in collaboration with the encoder 34 may detect whether a suitable length of substrate 13 has passed. The controller may use this information to control the rotational speed of the feed roll 16 and trigger the cutting element 20 to effect a cut of the material 11 between the cutting element 20 and the anvil roll 18 at the cut point 21. For each complete revolution of the anvil roll 18 and cutting element 20, a sensor, such as the second motor controller 158 detects the rotational position of the cutting element 20. The signal information from the sensor is used to update the controller as to the exact position of the cutting element 20, such as the knife blade. The system controller continuously monitors and controls the rotational speed of the feed roll 16 and the anvil roll 18 and triggers the cutting element 20, in order for a cut of the material 11 to occur at the correct position for each substrate. Exactly when the cut gets made, relative to the position of the substrate 13 as it moves towards the nip between the applicator roll 22 and backup roll 26, defines where the each of the sections 12 get positioned on the substrate 13. The signal from the sensor 32 concerning the presence or absence on the conveyor of the substrate 13, the presence or absence of registry indicia displayed on the substrate 13, or the passage of a defined length of substrate 13 can also be used to automatically enable or disable the feed roll 16. In some instances, the anvil roll is configured to control a distance between consecutive sections of web material delivered to the applicator roll by controlling a delivery of the sections of web material from the anvil roll to the applicator roll. The anvil roll may advance a first section of web material to the applicator roll while the feed roll delays the feed of the web material to the anvil roll such that a distance is formed between the first section of web material and a consecutive section of web material. The system controller may coordinate the rotation of the feed roll and the anvil roll such that the anvil roll advances sections of web material while the feed roll controls the feed rate of the web material to the anvil roll.

An example of a suitable integrated control system (ICS) may be one sold under the trade name ControlLogix (available from Rockwell Automation of New Brighton, Minn.), or any suitable system that provides a logic control for the discrete, drives, motion, process and safety control such that the length of material applied and the location of the material on the substrate can be changed and controlled.

In some examples, a single production run may number in the thousands of individual substrates, which may be formed from, for example, paper, corrugated cardboard, nonwoven material, film, box blanks, or may be a continuous carton stock. If the sensor 32 detects an irregularity in a substrate feed sufficiently early, the controller can adjust the speed of the feed roll 16 and/or cutting element 20 to change the timing of the cut, and thus the positioning of the section 12 on the incoming substrate 13. Irregularities between substrates can happen between each substrate 13 within the same run. The system described herein can compensate for each irregularity to place each section 12 on the desired position on the substrate 13. Such adjustments can occur automatically during the single production run without having to stop the run to make a mechanical adjustment.

When beginning a production run that includes applying sections 12 of web material 11 on a substrate 13 or a plurality of substrates, such as a series of consecutive substrates, an operator may enter into the system controller information such as the length of each substrate 13, the desired length of each of the sections 12 to be applied, and a suitable location where the sections 12 are to be placed on the substrate 13. The length of each of the sections 12 and the location where the sections 12 are to be placed on the substrate 13 may be different for each production run, but the system 10 may be adjusted by changing the settings of the system controller without changing to a new feed roll 16 and/or anvil roll 18. The presently disclosed system is adjustable and can be adapted to apply defined sections 12 having a suitable length, at a suitable position on a substrate of any shape or size. The length of the sections 12 can be changed without requiring replacing or changing the components of the system. For example, controlling the feed rate of the material from the feed roll 16 to the anvil roll 18 and/or the timing of the cutting of the web material 11 can control the length of the sections 12 without having to change between feed rolls, anvil rolls, or cutting elements of different diameters.

In some embodiments, the system 10 can be used to apply a web material 11 that is elastic while controlling the web material 11 from releasing from the components of the system 10. In certain instances, it is desirable to cut and apply sections 12 of defined lengths of material, such as tape, that is constructed from an elastic material. In general, elastic materials can be deformed when a force such as a tensile or compressive force is applied to the material. For example, when a tensile force is applied to an elastic material in a first direction, the elastic material may stretch, or increase in length, in the first direction. When the tensile force is released, the elastic material will seek to retain its original size and/or shape, and thus retracts along the first direction. When the elastic material is stretched, the elastic material may build up potential energy which is stored by the elastic material. When the tension is released and the elastic material snaps back to its original size, often the potential energy stored by the elastic material is great enough to cause the elastic material to overcome additional forces that are applied to the elastic material, such as a force that is holding the material in position. In a further example, if a material having a first length in a first direction is pulled along the first direction, the material may stretch in the first direction to a size greater than the first length. If the material is cut in a direction perpendicular to the first direction, for example to form two separate pieces of material, while the material is stretched, each piece of material may snap away from each other along the first direction. When an elastic material, such as tape, is cut using a system that causes elastic deformation of the elastic material, cutting the elastic material while it is elastically deformed may result in the material snapping back when cut and may result in the material being released from the system.

For example, in the system 10 shown in FIG. 1 the tangential speeds of the feed roll 16 and anvil roll 18 are configured to control the linear speed of the material 11 at certain points along a predetermined path through the system 10. Differences in the tangential speeds of the feed roll 16 and the anvil roll 18 may stretch or compress the web material 11, such as along a portion of the web material 11 that extends between the feed roll 16 and the anvil roll 18. For example, if the tangential speed of the feed roll 16 and the tangential speed of the anvil roll 18 are the same, the tension in the material will be low along the portion of the web material 11 that extends between the feed roll 16 and the anvil roll 18. As the tangential speed of the feed roll 16 decreases with respect to the tangential speed of the anvil roll 18, the anvil roll 18 starts to pull the web material 11 from the feed roll 16, and applies tensile force in the web material 11 along the portion of the web material 11 extending between the feed roll 16 and the anvil roll 18. When the tangential speed of the feed roll 16 increases with respect to the tangential speed of the anvil roll 18 the tensile force applied to the portion of the web material 11, for example, the portion of web material 11 extending between the feed roll 16 and the anvil roll 18, decreases.

If the cutting element 20 cuts the web material 11 when the web material 11 is elastically deformed, for example, when a portion of web material 11 is stretched in the direction between the feed roll 16 and the anvil roll 18, the web material 11 may snap back once the cut is completed. This may cause the web material 11 to pop off from the anvil roll 18 and/or feed roll 16. This result may occur in instances where the feed roll 16 is rotating with the outer surface 17 moving at a slower speed than the speed of the outer surface 19 of the anvil roll 18 at the moment when, or just before when, the web material 11 is being cut. Because the outer surface 19 of the anvil roll 18 is moving faster than the outer surface 17 of the feed roll 16, the anvil roll 18 may pull the web material 11 from the feed roll 16. If the web material 11 is elastic, it will stretch when pulled. If the cut is made when the web material 11 is stretched, for example stretched along the portion of the web material 11 that is moving from the feed roll 16 to the anvil roll 18, the web material 11 will spring back or snap back because of elastic recovery. In some instances, this spring back causes the web material 11 to separate from the feed roll 16, and/or the anvil roll 18. This spring back may result in the web material 11 or the sections 12 separating from the defined path through the system 10. For example, the sections 12 may spring back to retain the original length causing them to snap off and separate from the surface of the anvil roll 18. Having the web material 11 or sections 12 snap off the feed roll 16, the anvil roll 18, or away from the predetermined path, may lead to interruptions during operation, as the system 10 has to be reset to feed the web material 11 back into position in the system 10, and may also result in production defects. In further examples, a difference in speed between the cutting element 20 and the anvil roll 18 can result in a mismatched tangential speed at the moment the cut is made. If the cutting element 20 is traveling faster than the anvil roll 18, the cutting element 20 may pull and stretch the web material 11, causing it to snap back when it is cut and may cause it to separate from the predetermined path.

The systems and methods disclosed herein can be used to cut elastic material into sections of defined lengths while maintaining the material substantially free of elastic deformation during the cutting of the material. A material that is substantially free of elastic deformation refers to a condition where a dimension, such the shape, of the material is substantially the same as what the material would be in if the material were in a relaxed state, for example free from tensile or compressive forces on the material. For example, various elastic materials may change shape and/or size in response to external forces being applied to the elastic material. Forces such as tension or compression applied to the elastic material may cause the elastic material to stretch or compress in response. As used herein "substantially free of elastic deformation" is defined as a condition wherein a material is not deformed more than about 10 percent greater than the material would be in its relaxed state. For example, for a length of material that is 1 centimeter in length in a first direction when no external forces are applied to the material along the first direction, the material is substantially free of elastic deformation when the material is from about 0.9 cm. to about 1.1 cm. in length in the first direction. In a preferred embodiment, a material cut using the system described herein is not stretched more than from about 3 percent to about 6 percent greater than the material would be in its relaxed state. It is also envisioned that the systems disclosed herein may also be useful for applying web materials that are not elastic.

The presently disclosed methods and systems are useful to cut and apply a wide range of material to various kinds of substrates. The material may include, but is not limited to, various ribbon materials, various web materials, and various widths and lengths of material. The materials may include films, non-woven materials, paper materials, composite or laminated tapes, tapes with adhesives, tear tapes or reinforcement tapes such as those sold under the trade names Sesame® or Enforcer® (available from H.B. Fuller Company, located in St. Paul, Minn.). The web, film or fiber may comprise polymeric material, polyester, polypropylene, polyethylene, polyamide (e.g., aromatic polyamide such as KEVLAR fiber from E.I. du Pont or nonaromatic polyamide such as nylon), fiberglass, natural fibers such as cotton or hemp, and/or other similar materials and combinations thereof. The substrate may be a cellulosic material selected from paper, a paper/polymeric film laminate, or a fiber-reinforced paper. The fibers of the substrate may be continuous strands (e.g., a multifilament yarn or a monofilament) unidirectionally oriented in a direction parallel to the length of the tape. In certain embodiments the fibrous material is polyester fiber. In certain embodiments, the carrier substrate is a single layer of material. The web materials may be coextrusions or laminations of a combination of these materials.

Further examples include flexible materials and that include an adhesive such as a hot melt adhesive, a pressure sensitive adhesive, a remoistenable adhesive, a heat activated adhesive, a hot melt pressure sensitive adhesive, moisture-curable hot melt adhesive, a hot melt remoistenable adhesive, a water dispersible hot melt adhesive, a biodegradable hot melt adhesive or a repulpable hot melt adhesive. Examples of these adhesives are any typical hot melt adhesive such as an ethylene-vinyl acetate copolymer (EVA-based) hot melt adhesive; EMA-based hot melt adhesive (ethylene methylacrylate); EnBA-based hot melt adhesive (ethylene n-butyl acrylate); hot melt adhesive based on polyamides; hot melt remoistenable adhesive based on polyamides and copolyesters; hot melt adhesives based on polyethylene and polypropylene homopolymers, copolymers and interpolymers, rubbery block copolymer hot melt adhesives; or RF (radio frequency) activatable adhesives.

The material, for example, may generally be an adhesive tape comprising a backing of about 2 mils (0.05 mm) to about 12 mils (0.31 mm) in thickness for example, and comprised of a polymeric material such as polyester, polypropylene, polyethylene, and combinations thereof. In further examples, the backing may be a cellulosic material such as paper, a paper/polymeric film laminate, or a fiber-reinforced paper. In one particular example, a tape with a coating of adhesive is applied to a substrate such as, for example, a paper product.

The material may be a tape placed used to form a carton or a box of cardboard, and/or may be a reinforcing tape and which may be in a position to reinforce a carrying handle, for example, on the finished carton. The tape, for example, may generally be an adhesive tape comprising a backing comprised of a polymeric film including polyester, polypropylene, polyethylene, and mixtures thereof. Alternatively, the backing may be a cellulosic material selected from paper, a paper/polymeric film laminate, or a fiber-reinforced paper.

The substrate that the material may be applied to may be a discrete unit such as a carton blank, or may be a substrate having a continuous length, such as a length of cardboard, wood, woven material, non-woven material, etc. that is greater than the circumference of the applicator roll. For example, the substrate may include films, non-woven webs, paper products, paper board, carton blanks, box board, corrugated board, and other sheet materials and web materials, all of various widths and lengths. In some examples, the length of substrate may be divided or cut after having material applied. The length of material applied to a discrete unit can extend the full length of the discrete unit of substrate or can be applied only to a portion of the length of the discrete unit of substrate. The length of material may be applied at a pitch ratio related to the length of the substrate and the position of the length of material to the substrate.

In some embodiments, the substrate may be any of a variety of materials that tapes may be applied to, including but not limited to nonwoven material, paper, cardboard, or woven material. The substrate may be a diaper material or a polywoven bag. The substrate may be corrugated paper board. The corrugated board substrate may include an exterior liner and a corrugated member. In some implementations, the corrugated member consists of a series of parallel flutes. In other implementations, the corrugated member can include other configurations, such as a waffle-type pattern or honeycomb. The corrugated paper board may be a single wall structure (i.e., includes a single fluted corrugated medium and at least one liner layer) or a multiwall structure (i.e., includes at least two fluted corrugated mediums and at least one liner layer). One or more substrates can form an article of manufacture such as a packaging container. Examples of packaging containers include cartons and boxes, such as cartons for holding beverages (for instance, a hand-carry carton that holds six, 12 or 24 bottles or cans of a beverage), meat and produce bulk bins, wet-packed containers, reusable containers, rubber and chemical bulk bins, heavy duty containers, bags, electronics and envelopes. A continuous corrugated board substrate can be manufactured by bonding the corrugated member to the exterior liner using an adhesive, and subjecting the exterior liner and corrugated member to heat.

The material can be applied to the substrate at a wide range of substrate speeds, and may be applied as part of a continuous process, such as while the length of web material and/or the substrate is fed to the system at a constant feed rate from a feed source. According to certain examples, the substrate speed may be from about 61 meters (200 ft.), or about 183 meters (600 ft.), to about 305 meters (1000 ft.), or about 366 meters (1200 ft.) per minute or higher, or a speed between any pair of the foregoing values, although additional speeds are contemplated. In a further example, the substrate may be carton blanks with at least one section of web material to be applied to each carton blank. The system may be useful to apply a section of web material to the surface of the carton blanks at speeds of 10,000 cph (cartons per hour), 20,000 cph, or as great as 30,000 cph. The web material may be cut and applied to the substrate as part of an intermittent process, such as a process that includes starting and stopping the feed rate of the web material as it is fed to the system from a feed source. For example, the system may be operated to apply web material to a substrate, with time between when a first section of web material is being applied and when a subsequent section of web material is being applied.

EXAMPLES

The following non-limiting examples are included to further illustrate various embodiments of the present disclosure and do not limit the scope of the present disclosure.

Example 1

Figure 10:
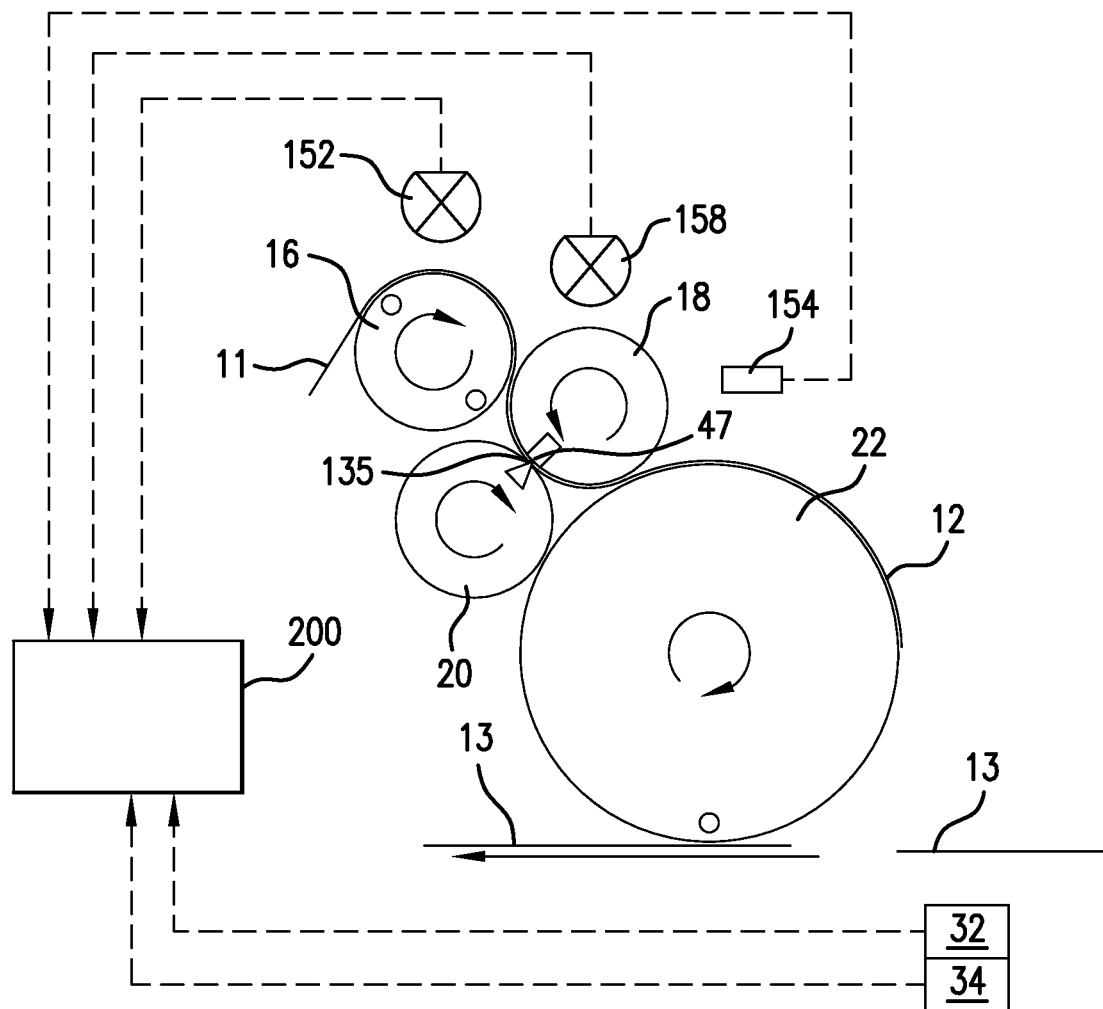
FIG. 10 is a front view of certain components of the system shown in FIG. 1 in operation, in accordance with some embodiments.

FIG. 10 is a general schematic of the system 10 previously described with reference to FIG. 1 to describe a process for operating the system 10 according to certain embodiments. The process described herein may be used to cut and apply web material 11, including web material 11 that is elastic, into sections 12 having a length that is governed by the feed roll 16, independent of the circumference of the anvil roll. The system 10 helps to reduce tension in the web material 11 at the point when the web material 11 is cut, by coordinating the tangential speed of the outer surface of the feed roll 16 to feed the desired amount of web material 11 and match the tangential speed of the outer surface of the anvil roll 20 at point of cut. The process can also be used to control the placement of each section 12 applied to the substrate, and the gap between consecutive sections 12 of material to align with the desired location on the substrate governed by the anvil roll 18.

As shown in FIG. 10, the system 10 includes the feed roll 16, the anvil roll 18, the cutting element 20, the applicator roll 22, the anvil 47, the cutting feature 135, and the first, second, and third motor controllers 152, 158, and 164 respectively, previously described with respect to FIGS. 1 and 9. As also shown in FIG. 10, the system includes a system controller 200 which is in communication with the sensor 32, the encoder 34, and the first, second, and third motor controllers 152, 158, and 164. The first motor controller 152 is coupled to the feed roll 16. In some examples, the first motor controller 152 may be a servo drive. The feed roll 16 rotates to advance a defined length of web material 11 to the anvil roll 18. The feed roll 16 advances the web material 11 along a predetermined path defined along the outer surface of the feed roll 16 to the outer surface of the anvil roll 18 which receives the web material 11 from the feed roll 16. The first motor controller 152 controls the rotational speed of the feed roll 16 which allows the system to vary the tangential speed of the feed roll 16, rather than being restrained to a fixed speed.

As shown, the cutting element 20 comprises a rotary knife and is located proximate to the anvil roll 18 such that the outer surface of the anvil roll 18 and the rotary knife come in contact with each other in a synchronized fashion to cut the web material 11 into sections 12 that will be applied to the substrate 13. The feed roll 16 and anvil roll 18 have separate drive means, such as the first and second motors 150, 156 shown in FIG. 9, which allows the tangential speed of the feed roll 16 to change in relation to the tangential speed of the anvil roll 18. The speeds can be adjusted by the controller 200 so the length of the sections 12 applied and the location of each of the sections 12 on the substrate 13 can be controlled during operation. The tangential speed of the feed roll 16 is coordinated to the tangential speed of the anvil roll 18 by the controller such that at the point of cut, the web material 11 is level against the anvil roll 18, which avoids the web material 11 from being bowed or wrinkled during the cut. The second motor controller 158 controls the speed of the anvil roll 18 and the cutting element 20 to provide the applicator roll 22 with cut sections 12 of web material 11 and a suitably sized gap between consecutive sections 12 such that the applicator roll 22 positions each of the sections 12 at a predetermined location on the substrate 13. The components of the system 10, are configured to continuously feed information to the controller 200 which can be programmed to adjust the drive speeds of the drive motors to cut the web material 11 into sections 12 of suitable length and form a suitably sized gap between consecutive sections 12 on the applicator roll 22.

In this example, the circumference of the feed roll 16, anvil roll 18, and cutting element 20 are each the same. For example, each may be about 51 cm (20 inches). The cutting element 20 and anvil roll 18 are fitted with one cutting feature 135 and one anvil 47 respectively, thus there will be one cut per revolution of the anvil roll 18 and cutting element 20. In this example, the circumference of the applicator roll 22 is 122 cm (48 inches). The job space is on average 56 cm (22 inches) long. The job space is defined as the distance between repeated positions on the substrate 13, which distance also correlates to the distance between each section 12. For example, the job space may be the leading edge of a first carton blank to the leading edge of a consecutive second carton blank if the substrate 13 is comprised of individual cartons blanks. Carton blanks are flat pieces of material that may be cut and folded to form a carton. The length of each carton blank may be less than the job space, leaving a gap between consecutive carton blanks, but each carton blank may be equal to or longer than the sections 12 of web material 11 applied on each carton blank. If the linear speed of the substrate 13 and the tangential speed of the applicator roll 22 are the same, for this given geometry, the applicator roll 22 revolves a half a revolution for each job space.

In operation, the sensor 32 detects the substrate 13 position and the encoder 34 detects the speed in relation to the system 10 and feeds this data to the controller 200. In some examples, the controller 200 can match the tangential speed of the applicator roll 22 to the linear speed of the substrate 13. The anvil roll 18 and cutting element 20 are controlled to provide sections 12 of web material 11 along the applicator roll 22 to apply the tape at the desired position on the substrate 13. The controller 200 coordinates the rotation of the feed roll 16 and the anvil roll 18 to advance material 11 and cut it into sections 12, and may reduce the tangential speed of the feed roll 16 to cut the desired tape length. In some examples, if the desired length of each of the sections 12 is equal to the circumference of the feed roll 16 and anvil roll 18 the tangential speed of the feed roll 16 can be maintained at a constant rate. The speed of the anvil roll 18 may be controlled to provide gaps between consecutive sections 12 positioned on the applicator roll 12. The size of consecutive gaps may be different, and may be controlled by the speed of the anvil roll 18 in relation to the applicator roll 22. In some instances, the tangential speed of the applicator roll 22 can be greater than the tangential speed of the feed roll 16 and the anvil roll 18 to control the tension in the web material 11, for example to keep the web material positioned against the applicator roll 22.

FIG. 10 shows the system 10 at the point of cut, which is the point when the cutting element 20 and the anvil engage. The moment from one point of cut to the consecutive point of cut defines one cycle within the process. In this example, a defined section of web material of about 51 cm. (20 in.) long is to be cut. If the feed roll 16 rotates at a tangential speed of 51 cm. (20 in.) per second, the cutting element 20 and anvil roll 18 rotate at a tangential speed of 51 cm. (20 in.) per second. At this point in the cycle, the linear speed of the web material 11 is the same as the tangential speed of the knife roll 16 and the anvil roll 18, and each are at about 51 cm (20 inches) per second. For this example, there is typically no more than a small difference in tangential speed of the anvil roll 18 and the feed roll 16, throughout each cycle, and at the point of cut. The system 10 is programmed to apply consecutive sections 12, and the controller 200 can monitor and control the rotational speed of the feed roll 16 such that at the point of cut, the portion of the web material 11 along the outer surface of the feed roll 16 is the same as the portion of the web material along the outer surface of the anvil roll 18.

Figure 11:
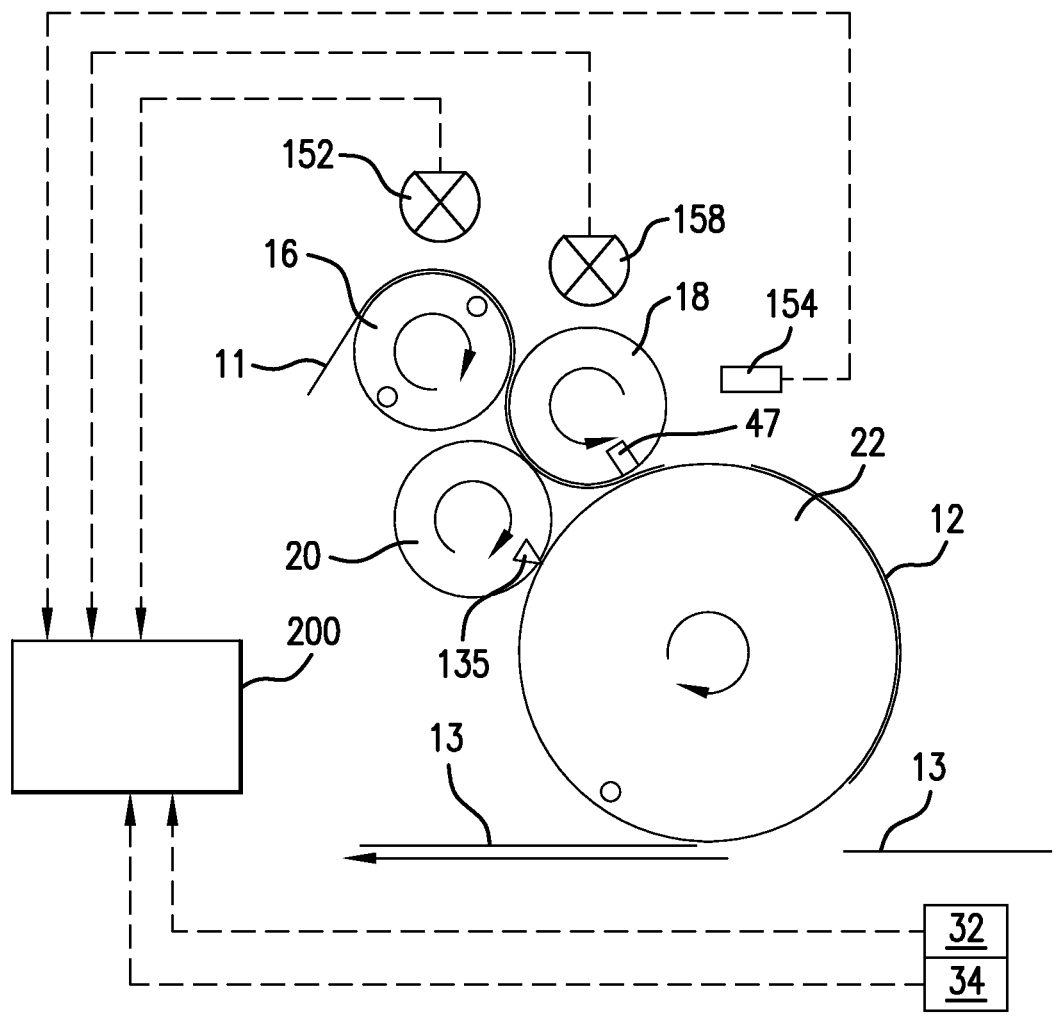
FIG. 11 is a front view of certain components of the system shown in FIG. 1 in operation, in accordance with some embodiments.

FIG. 11 shows the system 10 previously described with reference to FIG. 10, with the system 10 advanced farther along the same cycle after the point of cut. As shown in FIG. 11 after the point of cut, the controller 200 determines the passing of the cut sections 12 from the cutting element 20. After the point of cut, because the feed roll 16 and the anvil roll 18 have the same circumference which is the same as the length of each of the section 12, to form a gap in between consecutive sections 12, the system controller 200 can reduce the tangential speed of the feed roll 16 to hold the web material 12 and the anvil roll 18 speed can be reduced, to form the desired gap between consecutive sections 12 passed to the applicator roll 12. Alternatively, the applicator roll 22 can rotate faster than the speed of the feed roll 16 and the anvil roll 18 to form the gap between consecutive section 12, without slowing the feed roll 16 and anvil roll 18 between cuts.

Example 2

Figure 12:
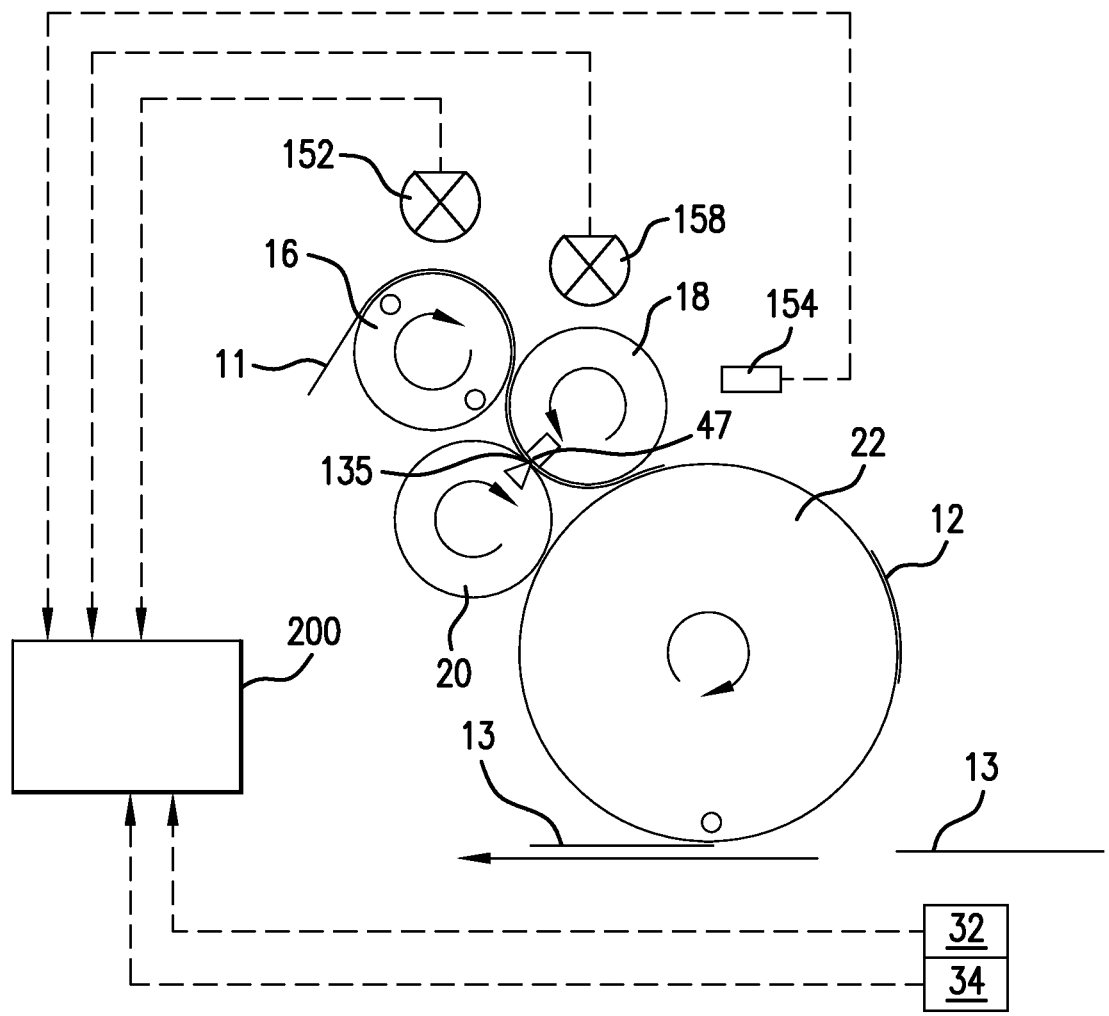
FIG. 12 is a front view of certain components of the system shown in FIG. 1 in operation, in accordance with some embodiments.

FIG. 12 shows various components of the system 10 previously described with reference to FIGS. 1 and 9, to describe a further example of the system 10 used to cut sections of web material having a length that is less than the circumference of the anvil roll 18. In this example, the circumference of the feed roll 16, the anvil roll 18, and cutting element 20 are the same. For example, the circumference of each of the feed roll 16, the anvil roll 18, and cutting element 20 may be about 46 cm. (18 in.). The cutting element 20 and anvil roll 18 are fitted with a single blade and anvil, thus there will be one cut per revolution of the anvil roll 18 and cutting element 20. In this example, the circumference of the applicator roll 22 is about 122 cm (48 inches), and the job space is on average about 61 cm. (24 in.) long. If the linear speed of the substrate 13 and the tangential speed of the applicator roll 22 are the same, for this given geometry, the applicator roll 22 revolves a half a revolution for each job space of 61 cm. (24 in.).

In general, the system 10 can cut sections 12 to any length that is less than the circumference of the anvil roll 18. That is, the system 10 is versatile to allow a user to cut sections 12 of web material 11 of various lengths, rather than being confined to cutting sections 12 that are equal to the circumference of the feed and/or anvil roll 16. Typically such an adjustment may require a separate feed and/or anvil roll 15 with a circumference for each length of web material 11 that a user may want. In this example, with these geometric configurations, to cut a 23 cm. (9 in.) length of web material 11 to be applied at a predefined location on the carton, requires a half revolution of the feed roll 16 to feed a 23 cm. (9 in.) section of web material 11 for each full revolution of the anvil roll 18 to cut that one section of web material 11. However, because the length of each section 12 to be cut is less than the circumference of the feed roll 16 and anvil roll 18 (which are equal in this example), to get the cutting feature 135 and the anvil 47 into position to cut the web material 11 at 23 cm. (9 in.), the feed roll 16 has to turn half a revolution for every rotation of the anvil roll 18. In other words, because the anvil roll 18 is being repositioned to create a gap between sections 12, and because the feed roll 16 is controlling the tape length, for a section of web material that is shorter than the circumference of the anvil roll 16, the feed roll 16 will have to slow down to prevent the web material from advancing while the anvil roll 18 turns to place the anvil 47 into position for the next cut.

In some embodiments, to get the anvil 47 into positon to cut the web material 11, in between points of cut, the feed roll 16 turns slower than the anvil roll 18. This may be accomplished by decreasing the tangential speed of the feed roll 16 in relation to the anvil roll 18. For example, if the feed roll 18 is rotating with a tangential speed of 23 cm. (9 in.) per second, the rotary knife and anvil roll 18 can be made to rotate such that the tangential speed is 46 cm. (18 in.) per second to get into position to cut a section 12 of web material 11 that is 23 cm. (9 in.), i.e. half the circumference of the feed roll 16. The leading edge of the web material 11 may remain engaged with the surface of the anvil roll 18 as the anvil roll 18 repositions. This helps the leading edge of the web material 11 to stay in position along the surface of the anvil roll 18 and be in place to be picked up by the anvil roll 18 and advanced for the next cut. In some instances, the outer surface of the anvil roll 18 experiences some slip in relation to the web material 11 while the feed roll 16 retains the web material 11 without the web material 11 slipping in relation to the outer surface of the feed roll 16.

For non-elastic materials, the material generally does not stretch as the anvil roll 18 rotates (i.e. the material is free from elastic deformation while the material is slipping in relation to the outer surface of the anvil roll 18) faster than the feed roll 16. However, for web material 11 that is elastic, because of some engagement between the outer surface of the anvil roll 18 and the web material 11, such as friction, this difference in tangential speed between the feed roll 16 and the anvil roll 16 may cause the web material 11 to stretch. This can also happen if the cutting feature 135 pulls on the web material as the cutting element 20 turns, causing the web material 11 to stretch. If the web material 11 is stretched at the point of cut (i.e. the moment the web material 11 is cut along its width), the web material 11 and the sections 12 may spring back after the point of cut, which may cause the web material 11 and the sections 12 to snap out of the predetermined path through the system 10.

For example, the web material 11 may snap off the outer surface of the feed roll 16 and/or the anvil roll 18. This is typically an undesirable result as the web material 11 may then need to be repositioned on the feed roll and/or the anvil roll. Also, the sections 12 may snap off the anvil roll 18. To help control the web material 11 from snapping off the feed roll 16 or the anvil roll 18, the system 10 can be configured such that at the point of cut, the web material 11 is substantially free of elastic deformation. In some embodiments, reducing elastic deformation of the web material at the point of cut may be accomplished by matching the tangential speed of the feed roll 16 to the tangential speed of the anvil roll 18 at the point of cut. The controller may match the rotational speed of the feed roll 16 such that tangential speed of the outer surface of the feed roll 16 matches, or is substantially the same as the tangential speed of the outer surface of the anvil roll 18 at the point of cut. This may be accomplished by having the rotation of the feed roll 16 slow down between cuts, and then accelerated before the point of cut to reach the cut speed, which is the speed of the feed roll 16 and the anvil roll 18 at the point of cut. Controlling the feed roll 16 to accelerate before the moment of cut such that tangential speed of the outer surface of the feed roll 16 matches the tangential speed of the outer surface of the anvil roll 18 at the point of cut results in the portion of web material 11 extended between and on the feed roll 16 and the anvil roll 18 to be free from elastic deformation at the point of cut.

For example, at the moment the web material 11 is cut, the tangential speed of the feed roll 16, the anvil roll 18, and cutting element 20 may be substantially the same (e.g. 18 in. per second). After the point of cut, the feed roll 16 can be slowed down to about ¼, about ⅓, or about ½ the tangential speed of the anvil roll 18 in order to retard the feed of the web material 11 from the feed roll 16 to the anvil roll 18. This may be the case when the anvil roll 18 is repositioning for the next cut. As an example, for about a 30 degree turn (1/12 turn) of the feed roll 16, the anvil roll can be controlled to complete a 90 degree turn (¼ turn). The feed roll 16 may be rotated at less than the anvil roll 18 while the anvil roll 18 completes about a 270 degrees turn (¾ turn) and the feed roll 16 completes about a 90 degree turn (¼ turn) in between cuts. Once the anvil roll 18 has rotated through about a 270 degree turn, the controller 200 accelerates the feed roll 16 such that the tangential speed of the feed roll 16 is substantially the same as that of the anvil roll 18 at the point of cut.

Figure 13:
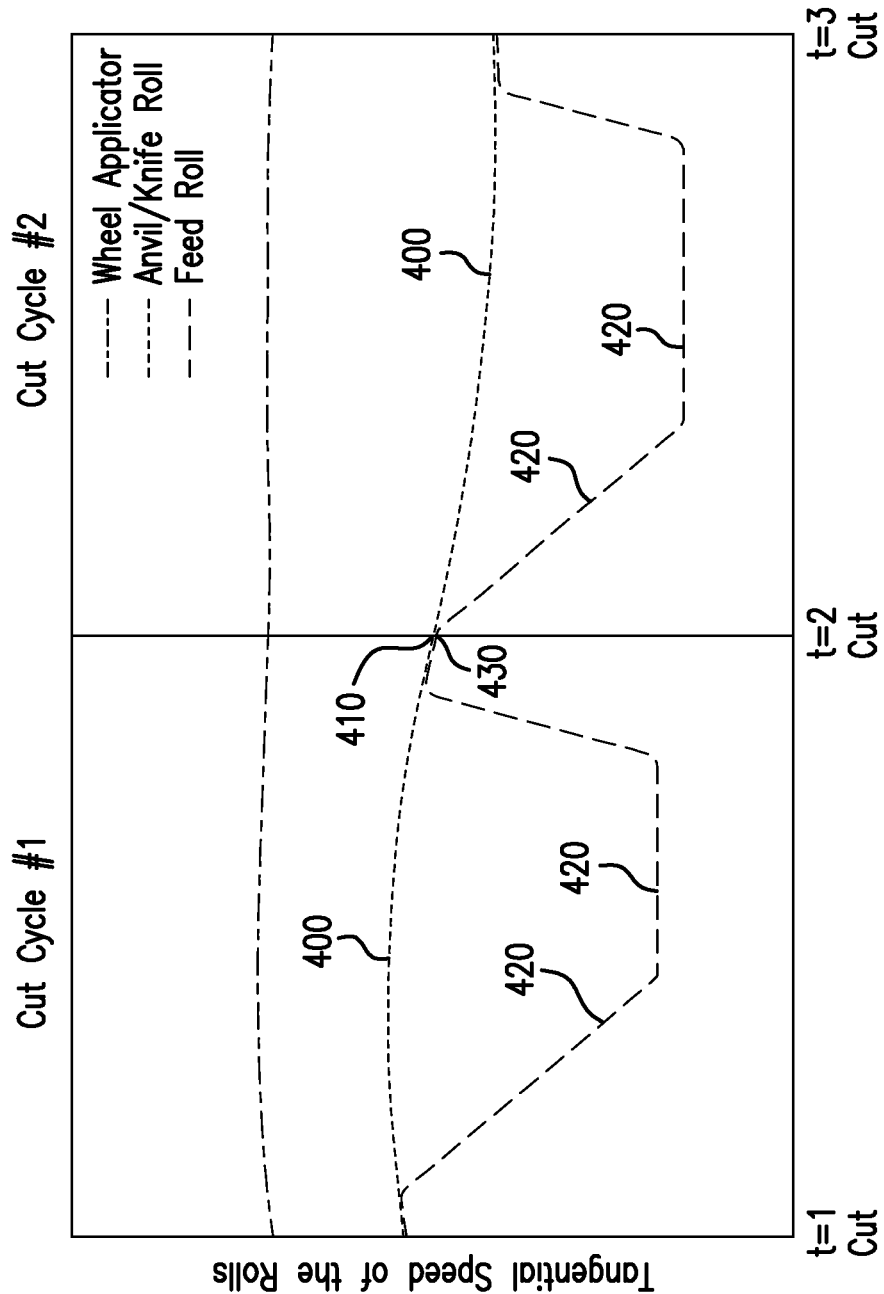
FIG. 13 is a graph showing an example speed profile of various elements of a material operation at various stages of operation, in accordance with some embodiments.

FIG. 13 is a graph of time versus tangential speed for various components of the system 10, as described with reference to FIG. 12. As shown in FIG. 13, the applicator roll rotates at a first tangential speed that is substantially constant throughout each cycle. The applicator roll turns such that its tangential speed is substantially the same as the linear speed of the substrate.

As shown in FIG. 13, the anvil roll rotates at a speed in between cuts that may be different than the speed at the point of cut. The speed of the anvil roll in between cuts is a first tangential speed 400 which may be faster or slower than the cut speed, for example to compensate for variations in the size of the gaps between consecutive substrates. The anvil roll first tangential speed 400 may be controlled such that the tangential speed of the anvil roll is slower than the applicator roll. This may form gaps between consecutive sections of web material as the sections are transferred from the anvil roll to the applicator roll. As shown in FIG. 13, at the point of cut point, the anvil roll is advancing at a second tangential speed 410, which is the cut speed. In some embodiments, the anvil roll second tangential speed 410 may be substantially the same as the first tangential speed 400, for example in instances where the circumference of the anvil roll is the same as the length of each section of web material that is being cut. In further examples, the first tangential speed 400 may be faster than the second tangential speed 410, for example, if the anvil roll needs to accelerate to reposition the anvil for the next cut. In some embodiments, the second tangential speed 410 may be slower than the first tangential speed 400, for example, if the system has detected a variation in spacing between consecutive substrates and needs to slow down to compensate.

As shown in FIG. 13, the feed roll rotates at a speed in between cuts that is different than the speed at the point of cut. The speed of the feed roll in between cuts is a first tangential speed 420. In this example, the first tangential speed 420 of the feed roll is less than the first tangential speed 400 of the anvil roll. That is, the tangential speed of the feed roll is slower than the tangential speed of the anvil roll in between points of cut. At the point of cut, the feed roll has a second tangential speed 430, which is the cut speed. To reduce elastic deformation in the web material at the point of cut, the second tangential speed 430 of the feed roll is substantially the same as the second tangential speed 410 of the anvil roll at the point of cut. This may be accomplished by accelerating the feed roll from the first tangential speed 420 to the second tangential speed 430 so that the speed of the outer surface of the feed roll is at the cut speed at the moment of cut. Having the tangential speed of the feed roll substantially the same as the tangential speed of the anvil roll at the point of cut helps reduce tension in the web material and helps inhibit the web material from being elastically deformed at the point of cut. As defined here with regard to the tangential speeds of the feed roll and the anvil roll, substantially the same is defined as a first speed that is within 5% of a second speed. That is, at the point of cut, the tangential speed of the feed roll is no greater than 5%, no greater than 3%, or no greater than 1% higher or lower than the tangential speed of the anvil roll.

Figure 14:
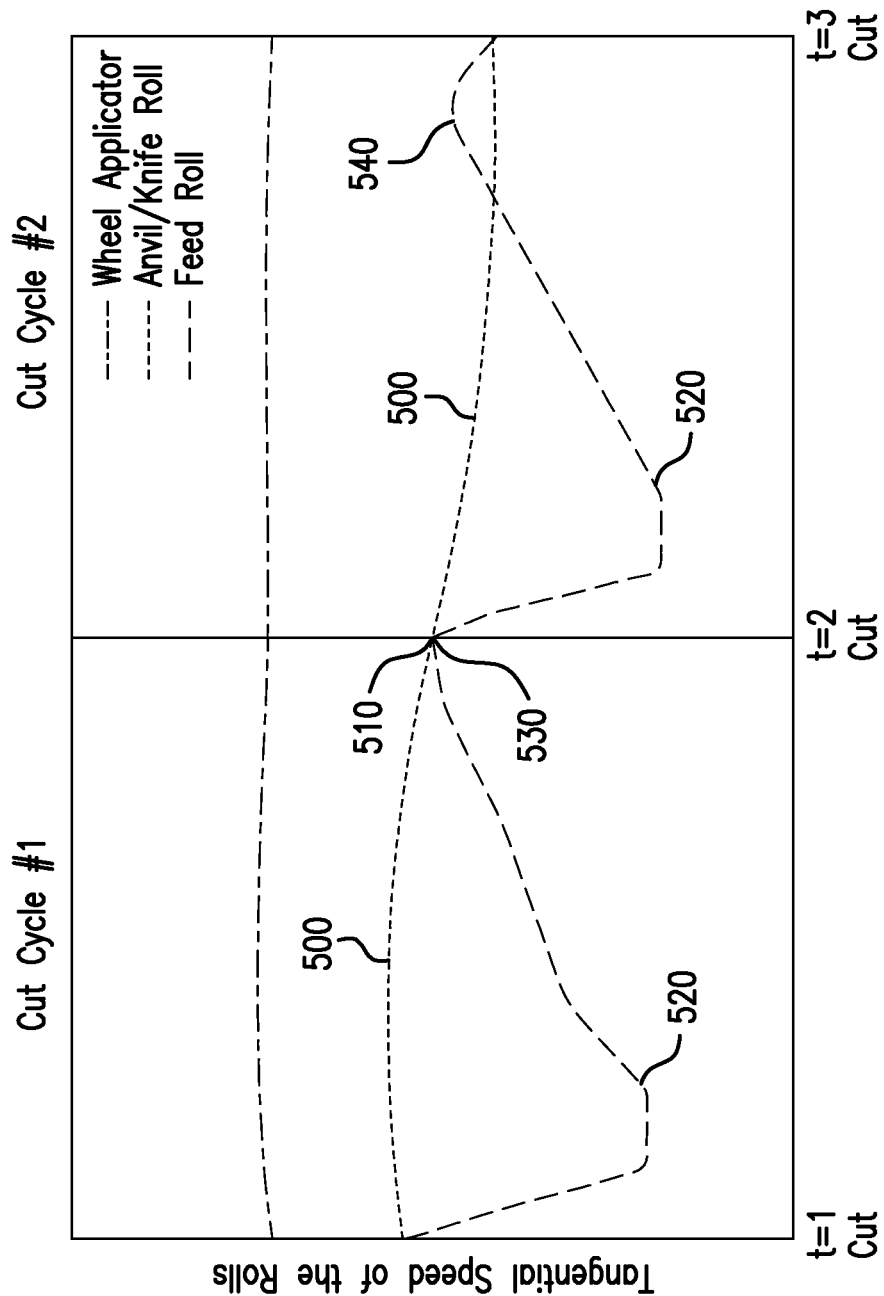
FIG. 14 is a graph showing an example speed profile of various elements of a material operation at various stages of operation, in accordance with some embodiments.

FIG. 14 is a graph of time versus tangential speed for various components of the system 10, as described with reference to FIG. 12, according to further embodiments. As shown in FIG. 13, the applicator roll typically rotates at a speed that is substantially constant throughout each cycle. The tangential speed of the outer surface of the applicator roll is generally substantially the same as the linear speed of the substrate.

As shown in FIG. 14, the anvil roll rotates at a first tangential speed 500 in between cuts. At the point of cut, the anvil roll may rotate at a second tangential speed 510. In some embodiments, the second tangential speed 510 may be substantially the same as the first tangential speed 500. In some embodiments, the second tangential speed 510 may be slower than the first tangential speed 500, for instance if the circumference of the anvil roll is greater than the length of each section of web material that is being cut. If the circumference of the anvil roll is greater than the length of each section of web material that is being cut, as the anvil roll may be allowed to slip in relation to the web material in between points of cut.

As shown in FIG. 14, the feed roll rotates at a first tangential speed 520 in between points of cut. As shown, the first tangential speed 520 of the feed roll is generally less than the first tangential speed 510 of the anvil roll such that the tangential speed of the outer surface of the feed roll is lower than the tangential speed of the outer surface of the anvil roll in between cuts. Before each point of cut, the feed roll accelerates from the first tangential speed 520 to a second tangential speed 530, which is the cut speed. The second tangential speed 530 of the feed roll is substantially the same as the second tangential speed 510 of the anvil roll at the point of cut.

As also shown in FIG. 14, at times between the points of cut, the feed roll can be made to rotate at a third tangential speed 540 that is higher than either the tangential speed of the anvil roll or the cut speed. However, at the point of cut, the tangential speed of the feed roll is substantially the same as the tangential speed of the anvil roll. For example, the third tangential speed 540 of the feed roll may be faster than the tangential speed of the anvil roll to decrease a tension in the web material. But the tangential speed of the feed roll is controlled such that the tangential speed of the outer surface of the feed roll is substantially the same as the tangential speed of the outer surface of the anvil roll at the point of cut. The system is versatile such that before or after the point of cut, the tangential speed of the outer surface of the feed roll may be higher or lower than the tangential speed of the outer surface of the anvil roll and/or the cut speed. This allows the various components to be controlled such that elastic deformation in the web material is inhibited at the point of cut. The system allows a user to control the web material as it passes through the system such that the system can apply cut sections of web material without losing control of the web material, such as by snapping off the feed roll or the anvil roll.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A system for applying a web material on a substrate, the system comprising:
    a feed roll defining a feed roll surface and configured to advance a web material along the feed roll surface;
    an anvil roll defining an anvil roll surface and configured to receive the web material from the feed roll along the anvil roll surface and provide a section of web material having a defined length at an anvil roll surface speed;
    a cutting element configured to cut the web material along the anvil roll surface to form the section of web material; and
    a first control element configured to control a speed of the outer surface of the feed roll between a first feed roll surface speed that is slower than the anvil roll surface speed and a second feed roll surface speed that is substantially the same as the anvil roll surface speed before the cutting element cuts the web material.

2. The system of claim 1, wherein the feed roll is configured to control a feed rate of the web material from the feed roll to the anvil roll such that the web material is substantially free of elastic deformation along a portion of the web material extending between the feed roll and the anvil roll as the cutting element cuts the web material.

3. The system of claim 1, wherein the first feed roll surface speed and the second feed roll surface speed are configured such that the web material is substantially free of elastic deformation along a portion of the web material extending between the feed roll and the anvil roll as the cutting element cuts the web material.

4. The system of claim 1, wherein the feed roll is configured to control a feed rate of the web material from the feed roll to the anvil roll such that the feed roll controls the defined length of the section of web material.

5. The system of claim 1, further comprising an applicator roll configured to receive the section of web material from the anvil roll and apply the section of web material to a surface of a substrate.

6. The system of claim 5, wherein the first control element is configured to define a distance between consecutive sections of web material delivered to the applicator roll by controlling advancement of the web material along the feed roll surface to the anvil roll surface.

7. The system of claim 1, further comprising a first drive element configured to drive the feed roll, and a second drive element configured to drive the anvil roll independent of the feed roll.

8. The system of claim 7, wherein the first control element is configured to control the first drive element, and further comprising a second control element that is configured to control the second drive element independent of the first control element.

9. The system of claim 8, wherein the feed roll is configured to be driven independent of the anvil roll and is configured to cooperate with the anvil roll to provide sections of web material having a defined length.

10. A system for applying a web material along a substrate, the system comprising:
    a feed roll defining a feed roll surface and configured to advance a web material along the feed roll surface to an anvil roll defining an anvil roll surface and configured to receive the web material from the feed roll surface and deliver a section of web material;
    a cutting element located proximate the anvil roll and configured to cut the web material to form the section of web material; and
    a first control element configured to cycle a speed of the outer surface of the feed roll between a first feed roll surface speed that is slower than the anvil roll surface speed and a second feed roll surface speed that is substantially the same as the anvil roll surface speed before the cutting element cuts the web material.

11. The system of claim 10, wherein the first control element is configured to control a feed rate of the web material from the feed roll to the anvil roll by controlling a tangential speed of the outer surface of the feed roll.

12. The system of claim 10, wherein the first control element is configured to control a feed rate of the web material from the feed roll to the anvil roll such that the portion of web material extending between the feed roll and the anvil roll is substantially free of elastic deformation as the cutting element is cutting the web material.

13. The system of claim 10, wherein the first control element is configured to control the rotational speed of the feed roll such that the feed roll surface cycles between a first tangential speed that is less than a tangential speed of the anvil roll surface immediately after the cutting element cuts the web material to form the section of web material, and a second tangential speed that is substantially the same as the tangential speed of the anvil roll surface as the cutting element is cutting the web material.

14. The system of claim 10, wherein the system is configured to cut an elastic web material into sections of elastic web material having a defined length with the elastic web material free of separation from a predetermined path between the feed roll and the anvil roll.

15. The system of claim 10, further comprising a first drive element configured to drive the feed roll, and a second drive element configured to drive the anvil roll independent of the feed roll.

16. The system of claim 15, wherein the first control element is configured to control the first drive element, and further comprising a second control element that is configured to control the second drive element independent of the first control element.

17. The system of claim 10, wherein the first control element is configured to control a feed rate of the web material from the feed roll to the anvil roll, to define a distance between consecutive sections of web material.

18. The system of claim 10, further comprising an applicator roll configured to receive the section of web material from the anvil roll and apply the section of web material to a surface of a substrate.

19. The system of claim 18, wherein the first control element is configured to control a feed rate of the web material from the feed roll to the anvil roll that is less than a feed rate of the section of web material from the anvil roll to the applicator roll, to define a distance between consecutive sections of web material.

\* \* \* \* \*